United States Patent
Tomioka et al.

(10) Patent No.: US 10,342,711 B2
(45) Date of Patent: Jul. 9, 2019

(54) TRANSPORT METHOD AND TRANSPORT DEVICE OF SINGLE-CUT SHEET ASSOCIATED WITH ABSORBENT ARTICLE

(71) Applicant: UNICHARM CORPORATION, Shikokuchuo-shi, Ehime (JP)

(72) Inventors: Masaharu Tomioka, Kagawa (JP); Toshihiro Mitani, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 15/765,066

(22) PCT Filed: Oct. 14, 2015

(86) PCT No.: PCT/JP2015/079012
§ 371 (c)(1),
(2) Date: Mar. 30, 2018

(87) PCT Pub. No.: WO2017/064763
PCT Pub. Date: Apr. 20, 2017

(65) Prior Publication Data
US 2018/0271713 A1    Sep. 27, 2018

(51) Int. Cl.
| | | |
|---|---|---|
| *A61F 13/15* | (2006.01) | |
| *A61F 13/49* | (2006.01) | |
| *B65H 35/08* | (2006.01) | |
| *B26D 1/143* | (2006.01) | |
| *B65H 29/24* | (2006.01) | |
| *B65H 39/14* | (2006.01) | |

(52) U.S. Cl.
CPC ........ *A61F 13/15764* (2013.01); *A61F 13/15* (2013.01); *A61F 13/15723* (2013.01);
(Continued)

(58) Field of Classification Search
CPC .......... A61F 13/15764; A61F 13/15804; A61F 13/15739; A61F 13/15723; A61F 13/49;
(Continued)

(56) References Cited

U.S. PATENT DOCUMENTS

2014/0102851 A1* 4/2014 Papsdorf ........... A61F 13/15764
198/411

FOREIGN PATENT DOCUMENTS

| CN | 104427961 A | 3/2015 |
|---|---|---|
| CN | 104812350 A | 7/2015 |

(Continued)

OTHER PUBLICATIONS

JP2002193440 (published Jul. 2002) Machine Translation of Description from EPO/Google.*
(Continued)

*Primary Examiner* — Christopher T Schatz
*Assistant Examiner* — Cynthia L Schaller
(74) *Attorney, Agent, or Firm* — Hauptman Ham, LLP

(57) ABSTRACT

A method of transporting single-cut sheets cut from a continuous sheet for absorbent articles includes transporting the sheets by bonding an upstream end of each sheet to an outer surface of a first rotating body by adhesive; and transporting the sheets by holding the sheets on an outer surface of a second rotating body rotating faster than the first body, the sheets being transported from the first body in a state in which the upstream end of each sheet is on the first body, a portion of each sheet on the second body sliding relative to the outer surface of the second body such that each sheet is transported at the peripheral speed of the first body, after the adhesive is separated and the upstream end moves to the second body, the second body transporting the sheets at the peripheral speed of the second body.

11 Claims, 8 Drawing Sheets

(52) U.S. Cl.
CPC .. *A61F 13/15739* (2013.01); *A61F 13/15804* (2013.01); *A61F 13/49* (2013.01); *B26D 1/143* (2013.01); *B65H 29/241* (2013.01); *B65H 29/243* (2013.01); *B65H 35/08* (2013.01); *B65H 39/14* (2013.01); *B65H 2301/3123* (2013.01); *B65H 2301/35* (2013.01); *B65H 2301/4451* (2013.01); *B65H 2301/5161* (2013.01); *B65H 2406/33* (2013.01); *B65H 2406/3454* (2013.01); *B65H 2701/194* (2013.01); *B65H 2801/57* (2013.01)

(58) Field of Classification Search
CPC ..... A61F 13/15; B65H 35/08; B65H 2801/57; B65H 2406/33; B65H 2301/35
See application file for complete search history.

(56) References Cited

FOREIGN PATENT DOCUMENTS

| | | |
|---|---|---|
| EP | 2491906 A1 | 8/2012 |
| EP | 2612632 A1 | 7/2013 |
| JP | 8-52696 A | 2/1996 |
| JP | 2002-193440 A | 7/2002 |
| JP | 2004-33549 A | 2/2004 |
| JP | 2007-508220 A | 4/2007 |
| JP | 2012-45317 A | 3/2012 |
| JP | 2012-91918 A | 5/2012 |

OTHER PUBLICATIONS

Extended European Search Report in EP Application No. 15906227.2, dated Aug. 29, 2018, 5pp.
International Preliminary Report on Patentability in PCT Application No. PCT/JP2015/079012, dated Apr. 26, 2018, 14pp.
Office Action in CN Application No. 201580083929.8, dated Aug. 24, 2018, 5pp.
International Search Report in PCT Application No. PCT/JP2015/079012, dated Dec. 22, 2015, 4pp.

* cited by examiner

B-B CROSS SECTION

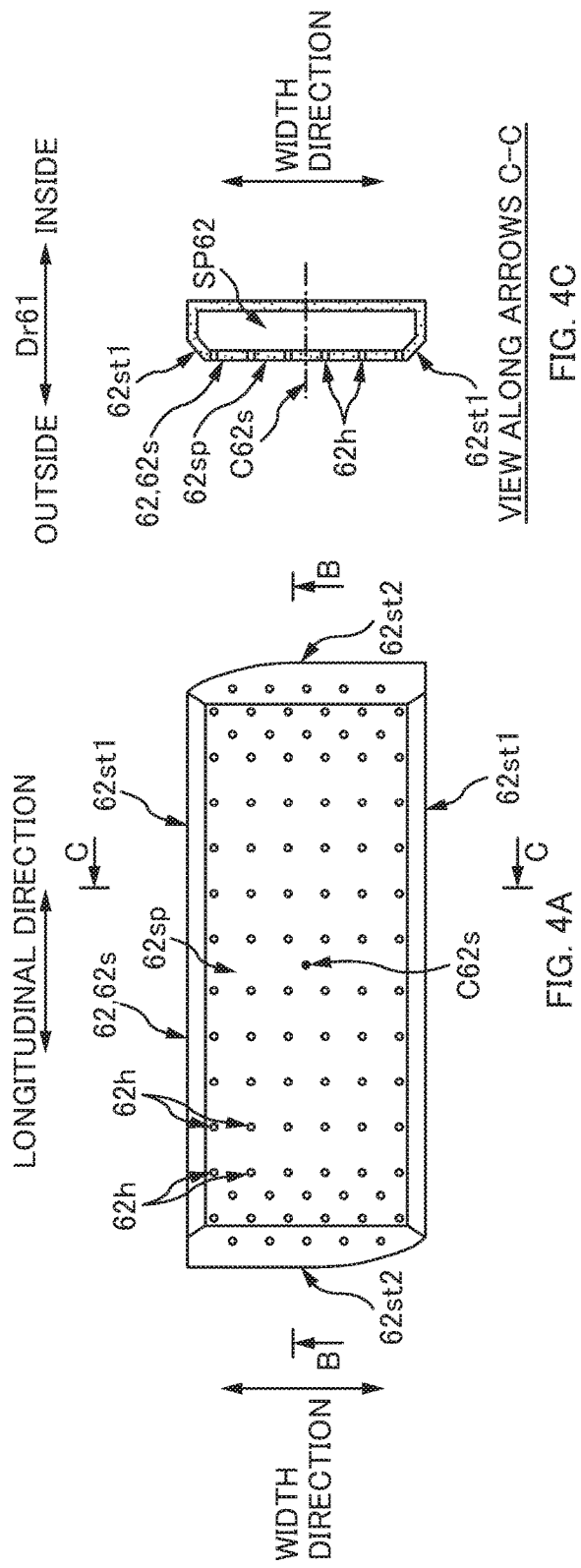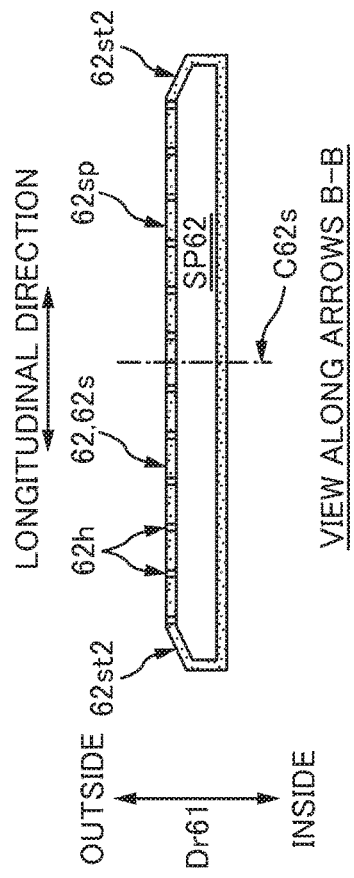

TRANSPORT METHOD AND TRANSPORT DEVICE OF SINGLE-CUT SHEET ASSOCIATED WITH ABSORBENT ARTICLE

RELATED APPLICATIONS

The present application is a National Phase entry of International Application No. PCT/JP2015/079012, filed Oct. 14, 2015.

TECHNICAL FIELD

The present invention relates to a transport method and a transport device of a single-cut sheet associated with an absorbent article such as a disposable diaper.

BACKGROUND ART

Conventionally, in a manufacturing line of absorbent articles such as disposable diapers, single-cut sheets each having a predetermined length are produced by being sequentially cut from a continuous sheet that is transported in a direction of transport, and a space between the produced single-cut sheets is enlarged to a target value for the subsequent processing (PTL 1).

CITATION LIST

Patent Literature

[PTL 1] Japanese Unexamined Patent Application Publication No. 2002-193440

SUMMARY OF INVENTION

Technical Problem

FIG. 1 is a schematic side view illustrating an example of an apparatus that performs such an enlargement process.

This apparatus includes an anvil roll $41a'$ that rotates along a direction of transport of a continuous sheet $10a'$, a cutter roll $41c'$ that is arranged to face the anvil roll $41a'$ and rotates, and a repitch roll $91'$ disposed at a predetermined position $P91'$ on the downstream side of the anvil roll $41a'$ in a direction of rotation $Dc41a'$ with respect to the arrangement position of the cutter roll $41c'$.

In this apparatus, first, the anvil roll $41a'$ rotates at a peripheral speed value $V41a'$ which is substantially equal to a transport speed $V10a'$ of the continuous sheet $10a'$ while sucking and holding on an outer circumferential surface $41as'$ the continuous sheet $10a'$ to be transported from the upstream step, thus transporting the continuous sheet $10a'$ taking the direction of rotation $Dc41a'$ as the direction of transport. Further, the cutter roll $41c'$ includes a cutter blade $41cc'$ on an outer circumferential surface $41cs'$ and rotates in conjunction with the anvil roll $41a'$. Then, the continuous sheet $10a'$ is cut each time the cutter blade $41cc'$ faces the outer circumferential surface $41as'$ of the anvil roll $41a'$, thereby producing a single-cut sheet $10'$ on the outer circumferential surface $41as'$ of the anvil roll $41a'$. This single-cut sheet $10'$ is transported taking the direction of rotation $Dc41a'$ as the direction of transport while being held on outer circumferential surface $41as'$ of the anvil roll $41a'$.

The repitch roll $91'$ is disposed at a predetermined position $P91'$ of the anvil roll $41a'$ in the direction of rotation $Dc41a'$. When each portion of the single-cut sheet $10'$ passes by the aforementioned predetermined position $P91'$, the each portion that has passed by is sequentially delivered from the outer circumferential surface $41as'$ of the anvil roll $41a'$ to the outer circumferential surface $91s'$ of the repitch roll $91'$. Accordingly, while receiving the single-cut sheet $10'$ on the outer circumferential surface $91s'$ and holding it on the outer circumferential surface $91s'$, the repitch roll $91'$ transports the single-cut sheet $10'$ with its own rotation taking the direction of rotation $Dc91'$ of the repitch roll $91'$ as the direction of transport.

Here, the peripheral speed value $V91'$ (m/s) of this repitch roll $91'$ is made larger than the peripheral speed value $V41a'$ (m/s) of the anvil roll $41a'$. Further, the anvil roll $41a'$ sucks and holds the single-cut sheet $10'$ in a substantially relatively immovable manner by the outer circumferential surface $41as'$. Thus, basically, as long as an upstream-side end part $10eu'$ of the single-cut sheet $10'$ is located on the outer circumferential surface $41as'$ of the anvil roll $41a'$, the single-cut sheet $10'$ is transported at the peripheral speed value $V41a'$ of the anvil roll $41a'$, so that the repitch roll $91'$ transports the single-cut sheet $10'$ while allowing a portion of the single-cut sheet $10'$ which is located on the outer circumferential surface $91s'$ of the repitch roll $91'$ to relatively slide behind in the direction of transport with respect to the outer circumferential surface $91s'$. After the upstream-side end part $10eu'$ of the single-cut sheet $10'$ moves from the outer circumferential surface $41as'$ of the anvil roll $41a'$ to the outer circumferential surface $91s'$ of the repitch roll $91'$, the repitch roll $91'$ transports the single-cut sheet $10'$ at a greater peripheral speed value $V91'$ of the repitch roll $91'$. Accordingly, a space $G10'$ between this single-cut sheet $10'$ and the single-cut sheet $10'$ which is adjacent on the upstream side and is cut to be produced is enlarged.

However, when the suction force of the outer circumferential surface $41as'$ of the anvil roll $41a'$ is not sufficient, the suction force may yield to sliding force directed to the downstream side which is imparted from the repitch roll $91'$ to the single-cut sheet $10'$. In that case, the single-cut sheet $10'$ slides on the outer circumferential surface $41as'$ of the anvil roll $41a'$ to the downstream side, and is shifted to the downstream side from the proper position. Then, the space $G10'$ between this single-cut sheet $10'$ and the single-cut sheet $10'$ located on the downstream side of this single-cut sheet $10'$ becomes smaller than the target value. That is, the enlargement of the space $G10'$ becomes insufficient. This may lead to deterioration in accuracy in the subsequent processing.

The present invention has been achieved in light of conventional problems such as those described above, and an object thereof is to reliably enlarge a space between the single-cut sheets adjacent one another in the direction of transport.

Solution to Problem

A main aspect of the invention for achieving the aforementioned object is a transport method of a single-cut sheet associated with an absorbent article, the method enlarging a space between single-cut sheets adjacent in a direction of transport, the single-cut sheets being produced by being sequentially cut from a continuous sheet that is transported in the direction of transport, the method including:

a first transporting step of transporting the single-cut sheets taking a direction of rotation of a first rotating body as the direction of transport by rotating the first rotating body while holding the single-cut sheets on an outer circumferential surface with a holding force of the outer circumferential surface of the first rotating body, the single-cut sheets being each produced by being cut from the continuous sheet; and a second transporting step of transporting the single-cut sheets taking a direction of rotation of a second rotating body as the direction of transport by rotating the second rotating body while receiving and holding the single-cut sheets on an outer circumferential surface of the second rotating body, the single-cut sheets being transported from the first rotating body, in the first transporting step, an upstream-side end part of each of the single-cut sheets in the direction of transport being bonded to the outer circumferential surface of the first rotating body by adhesive provided at least in a part of the upstream-side end part, each of the single-cut sheets being transported in the direction of transport at a peripheral speed value of the first rotating body, in the second transporting step, in a state in which the second rotating body rotates at a peripheral speed value larger than the peripheral speed value of the first rotating body, and the upstream-side end part of each of the single-cut sheets is located on the outer circumferential surface of the first rotating body, the second rotating body transporting each of the single-cut sheets while allowing a portion of each of the single-cut sheets located on the second rotating body to relatively slide behind in the direction of transport with respect to the outer circumferential surface of the second rotating body on the basis that each of the single-cut sheets is transported in the direction of transport at the peripheral speed value of the first rotating body, after the adhesive of the upstream-side end part is separated from the outer circumferential surface of the first rotating body and the upstream-side end part moves from the outer circumferential surface of the first rotating body to the outer circumferential surface of the second rotating body, the second rotating body transporting the single-cut sheets at the peripheral speed value of the second rotating body.

Further, another aspect of the invention for achieving the aforementioned object is a transport device of a single-cut sheet associated with an absorbent article, the device enlarging a space between single-cut sheets adjacent in a direction of transport, the single-cut sheets being produced by being sequentially cut from a continuous sheet that is transported in the direction of transport, the device including:

a first transport device that transports the single-cut sheets taking a direction of rotation of a first rotating body as the direction of transport by rotating the first rotating body while holding the single-cut sheets on an outer circumferential surface with a holding force of the outer circumferential surface of the first rotating body, the single-cut sheets being each produced by being cut from the continuous sheet; and a second transport device that transports the single-cut sheets taking a direction of rotation of a second rotating body as the direction of transport by rotating the second rotating body while receiving and holding the single-cut sheets on an outer circumferential surface of the second rotating body, the single-cut sheets being transported from the first rotating body, in the first transport device, an upstream-side end part of each of the single-cut sheets in the direction of transport being bonded to the outer circumferential surface of the first rotating body by adhesive provided at least in a part of the upstream-side end part, each of the single-cut sheets being transported in the direction of transport at a peripheral speed value of the first rotating body, in the second transport device, in a state in which the second rotating body rotates at a peripheral speed value larger than the peripheral speed value of the first rotating body, and the upstream-side end part of each of the single-cut sheets is located on the outer circumferential surface of the first rotating body, the second rotating body transporting each of the single-cut sheets while allowing a portion of each of the single-cut sheets located on the second rotating body to relatively slide behind in the direction of transport with respect to the outer circumferential surface of the second rotating body on the basis that each of the single-cut sheets is transported in the direction of transport at the peripheral speed value of the first rotating body, after the adhesive of the upstream-side end part is separated from the outer circumferential surface of the first rotating body and the upstream-side end part moves from the outer circumferential surface of the first rotating body to the outer circumferential surface of the second rotating body, the second rotating body transporting the single-cut sheets at the peripheral speed value of the second rotating body.

Other features of the present invention will be made clear by the description and attached drawings.

Advantageous Effects of Invention

According to the present invention, the space between the single-cut sheets adjacent one another in a direction of transport can be certainly enlarged.

BRIEF DESCRIPTION OF DRAWINGS

FIG. 4A is a schematic plan view when a holding pad 62 is seen from a holding surface 62s side, FIG. 4B is a view along arrows B-B in FIG. 4A, and FIG. 4C is a view along arrows C-C in FIG. 4A.

DESCRIPTION OF EMBODIMENTS

Figure 1:
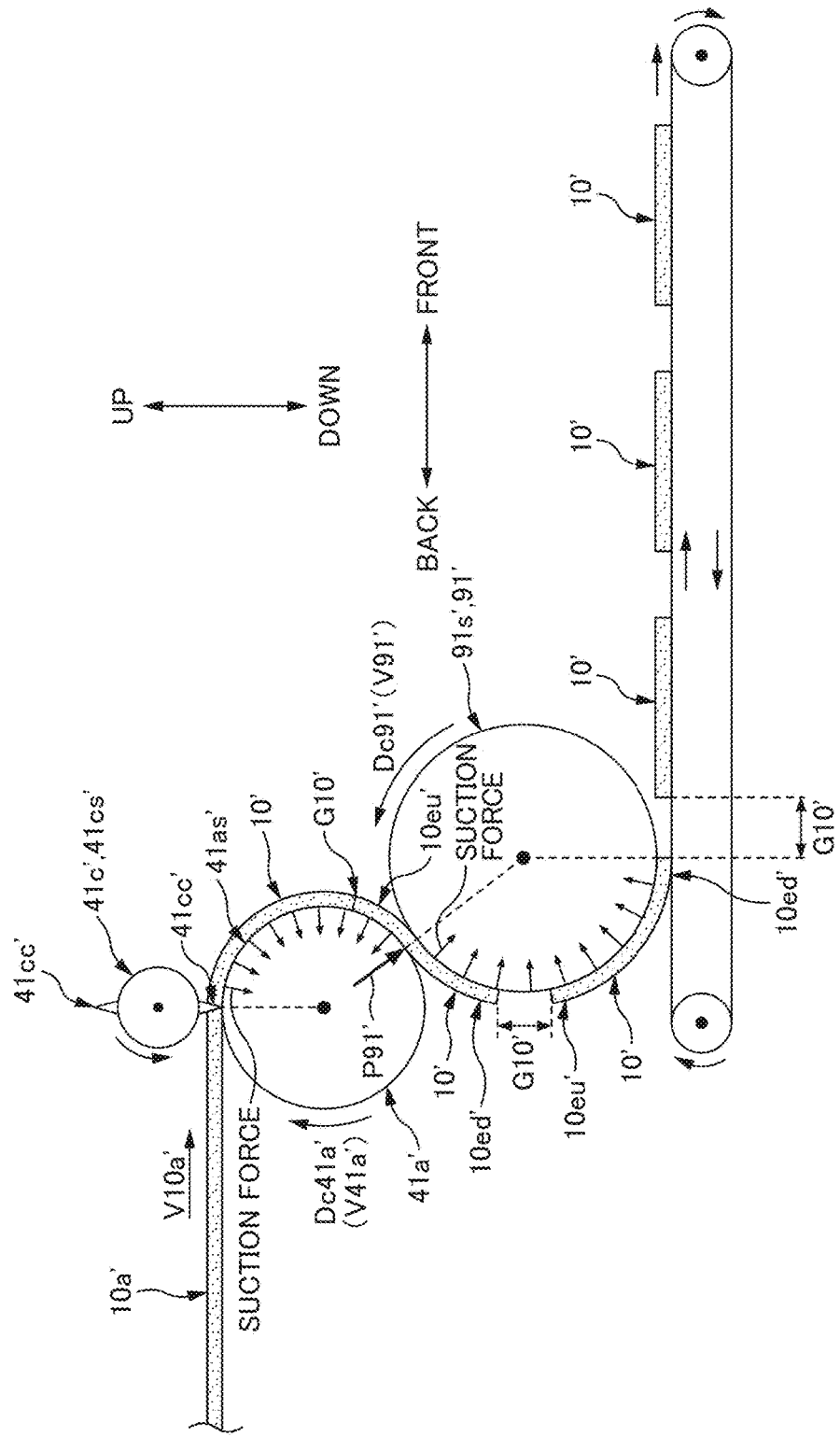
FIG. 1 is a schematic side view illustrating an example of an apparatus that performs an enlargement process of a space G10' between single-cut sheets 10', 10'.

At least the following matters are made clear from the description and drawings described below.

Disclosed is a transport method of a single-cut sheet associated with an absorbent article, the method enlarging a space between single-cut sheets adjacent in a direction of transport, the single-cut sheets being produced by being sequentially cut from a continuous sheet that is transported in the direction of transport, the method including:

a first transporting step of transporting the single-cut sheets taking a direction of rotation of a first rotating body as the direction of transport by rotating the first rotating body while holding the single-cut sheets on an outer circumferential surface with a holding force of the outer circumferential surface of the first rotating body, the single-cut sheets being each produced by being cut from the continuous sheet; and a second transporting step of transporting the single-cut sheets taking a direction of rotation of a second rotating body as the direction of transport by rotating the second rotating body while receiving and holding the single-cut sheets on an outer circumferential surface of the second rotating body, the single-cut sheets being transported from the first rotating body, in the first transporting step, an upstream-side end part of each of the single-cut sheets in the direction of transport being bonded to the outer circumferential surface of the first rotating body by adhesive provided at least in a part of the upstream-side end part, each of the single-cut sheets being transported in the direction of transport at a peripheral speed value of the first rotating body, in the second transporting step, in a state in which the second rotating body rotates at a peripheral speed value larger than the peripheral speed value of the first rotating body, and the upstream-side end part of each of the single-cut sheets is located on the outer circumferential surface of the first rotating body, the second rotating body transporting each of the single-cut sheets while allowing a portion of each of the single-cut sheets located on the second rotating body to relatively slide behind in the direction of transport with respect to the outer circumferential surface of the second rotating body on the basis that each of the single-cut sheets is transported in the direction of transport at the peripheral speed value of the first rotating body, after the adhesive of the upstream-side end part is separated from the outer circumferential surface of the first rotating body and the upstream-side end part moves from the outer circumferential surface of the first rotating body to the outer circumferential surface of the second rotating body, the second rotating body transporting the single-cut sheets at the peripheral speed value of the second rotating body.

According to such a transport method of a single-cut sheet associated with an absorbent article, the single-cut sheets are held on the outer circumferential surface of the first rotating body not only by the holding force of the outer circumferential surface of the first rotating body but also by the adhesive strength of at least a part of the adhesive of the aforementioned upstream-side end part. Accordingly, when the upstream-side end part of each of the single-cut sheets is located on the first rotating body, each single-cut sheet can be reliably held on the outer circumferential surface, thereby reliably transporting each single-cut sheet at the peripheral speed value of the first rotating body. Consequently, a portion of the single-cut sheet which is located on the second rotating body can certainly relatively slide behind in the direction of transport with respect to the outer circumferential surface of the second rotating body. As a result, a space between the single-cut sheet and the single-cut sheet which is adjacent on the downstream side can be reliably enlarged.

Further, such adhesive is provided at least in a part of the upstream-side end part of each of the single-cut sheets. Thus, the adhesive strength due to such adhesive can be imparted for substantially the entire period during which each single-cut sheet is held on the first rotating body. This also effectively contributes to the reliable enlargement described above.

In the transport method of a single-cut sheet associated with an absorbent article, it is preferable that the adhesive is provided at least in a most upstream-side part of each of the single-cut sheets in the direction of transport.

According to such a transport method of a single-cut sheet associated with an absorbent article, the aforementioned adhesive is provided at the most upstream side of each of the single-cut sheets, and thus the adhesive strength due to such adhesive can be reliably imparted for substantially the entire period during which each single-cut sheet is held on the first rotating body.

In the transport method of a single-cut sheet associated with an absorbent article, it is preferable that a cutter device that cuts the continuous sheet and transports the single-cut sheets to the first rotating body is provided at an upstream side position of the first rotating body in the direction of transport, the cutter device includes a third rotating body and a fourth rotating body which rotate along the direction of transport with their outer circumferential surfaces facing each other, while the third rotating body holds on the outer circumferential surface the continuous sheet that is transported in the direction of transport, a blade-shaped cutter blade provided so as to protrude from the outer circumferential surface of one of the third rotating body and the fourth rotating body is received by a surface-like receiving blade provided on the outer circumferential surface of another rotating body to produce the single-cut sheets by being cut from the continuous sheet on the outer circumferential surface of the one rotating body, the third rotating body transports the single-cut sheets to the first rotating body by rotating while holding the produced single-cut sheets on the outer circumferential surface, and the adhesive is applied to one of two surfaces of the continuous sheet, the one facing toward the outer circumferential surface of the fourth rotating body.

According to such a transport method of a single-cut sheet associated with an absorbent article, the adhesive is applied to one of two surfaces of the continuous sheet, the one facing toward the outer circumferential surface of the fourth rotating body. Accordingly, it is possible to allow such adhesive to reliably contribute to the holding of the absorbent main body on the outer circumferential surface of the first rotating body.

In the transport method of a single-cut sheet associated with an absorbent article, it is preferable that the fourth rotating body is a cutter rotating body including the cutter blade on the outer circumferential surface.

According to such a transport method of a single-cut sheet associated with an absorbent article, adhesive soiling of the adhesive which may occur in the cutter device can be easily cleaned. In other words, when the adhesive adheres to a surface-like receiving blade, the adhesive is less likely to be cleaned; however, in the aforementioned manufacturing method, the adhesive of the continuous sheet faces toward the cutter blade of the fourth rotating body, thereby allowing the adhesive to exclusively adhere to the cutter blade. Then, since the cutter blade has a blade shape, the adhesive soiling of adhesive can be relatively easily removed. Consequently, it is easier to clean the cutter device in general.

In the transport method of a single-cut sheet associated with an absorbent article, it is preferable that after a most upstream-side part of each of the single-cut sheets in the direction of transport moves from the third rotating body to the first rotating body, a most downstream-side part of each of the single-cut sheets in the direction of transport moves from the first rotating body to the second rotating body.

According to such a transport method of a single-cut sheet associated with an absorbent article, when each of the single-cut sheets moves from the first rotating body to the second rotating body, it is possible to allow each single-cut sheet not to straddle both the first rotating body and the third rotating body. Consequently, the single-cut sheet can be transported to the second rotating body exclusively based on only the rotating operation of the first rotating body. Thus, it can be prevented that the rotating operation of the third rotating body becomes a disturbance and accuracy of movement of the single-cut sheets to the second rotating body is deteriorated. Consequently, the space between the single-cut sheets can be enlarged with high accuracy.

In the transport method of a single-cut sheet associated with an absorbent article, it is preferable that a circumference length of the outer circumferential surface of the first rotating body is longer than a length of each of the single-cut sheets in the direction of transport.

According to such a transport method of a single-cut sheet associated with an absorbent article, since the circumference length of the first rotating body is made longer than the length of the single-cut sheet, when each single-cut sheet moves from the first rotating body to the second rotating body, it is possible to reliably prevent a state in which each single-cut sheet straddles both the first rotating body and the third rotating body.

In the transport method of a single-cut sheet associated with an absorbent article, it is preferable that the circumference length of the outer circumferential surface of the first rotating body is twice or more the length of each of the single-cut sheets in the direction of transport.

According to such a transport method of a single-cut sheet associated with an absorbent article, since the circumference length of the first rotating body is made twice or more the length of the single-cut sheet, when each single-cut sheet moves from the first rotating body to the second rotating body, it is possible to reliably prevent a state in which each single-cut sheet straddles both the first rotating body and the third rotating body.

In the transport method of a single-cut sheet associated with an absorbent article, it is preferable that the adhesive is provided also at least in a part of a downstream-side end part of each of the single-cut sheets in the direction of transport.

According to such a transport method of a single-cut sheet associated with an absorbent article, the single-cut sheet is held on the outer circumferential surface of the first rotating body also by the adhesive strength of at least a part of the adhesive provided in the downstream-side end part of each single-cut sheet. Thus, the single-cut sheets can be further reliably held on the outer circumferential surface of the first rotating body, thereby enabling the single-cut sheets to be reliably transported at the peripheral speed value of the first rotating body.

In the transport method of a single-cut sheet associated with an absorbent article, it is preferable that each of the single-cut sheets is produced by being cut at a predetermined position of the continuous sheet in the direction of transport, and the position to be cut is included in an applied region to which the adhesive is applied in the continuous sheet.

According to such a transport method of a single-cut sheet associated with an absorbent article, the aforementioned position to be cut is included in the applied region to which the adhesive is applied in the continuous sheet. Thus, the single-cut sheets produced by being cut at the aforementioned position to be cut are each provided with the adhesive in the upstream-side end part and the downstream-side end part in the direction of transport. Accordingly, the single-cut sheet in which the adhesive is provided in both end parts in the direction of transport can be easily and reliably produced.

Furthermore, according to this manufacturing method, the adhesive is also provided to the most upstream-side part of each of the single-cut sheets. Consequently, the adhesive strength due to such adhesive can be reliably imparted over substantially the entire period during which each single-cut sheet is held by the first rotating body.

In the transport method of a single-cut sheet associated with an absorbent article, it is preferable that a fifth rotating body rotating along the direction of transport is disposed so as to allow an outer circumferential surface of the fifth rotating body to face the outer circumferential surface of the first rotating body, and while the continuous sheet that is transported in the direction of transport is held on the outer circumferential surface of the first rotating body, a cutter blade provided so as to protrude from the outer circumferential surface of one of the first rotating body and the fifth rotating body is received by a surface-like receiving blade provided on the outer circumferential surface of another rotating body so that the single-cut sheets are produced by being cut from the continuous sheet.

According to such a transport method of a single-cut sheet associated with an absorbent article, the first rotating body can function as a cutter rotating body having a cutter blade or as an anvil rotating body having a surface-like receiving blade that receives the cutter blade of the cutter rotating body. With such a configuration, one of the cutter rotating body and the anvil rotating body can be omitted. Consequently, it is possible to simplify the device configuration.

In the transport method of a single-cut sheet associated with an absorbent article, it is preferable that the holding force of the first rotating body occurs due to a suction operation of a plurality of suction holes formed on the outer circumferential surface, and in a part of the outer circumferential surface to which the upstream-side end part of each of the single-cut sheets faces, the suction holes are not provided on an upstream side of a portion facing to the adhesive.

According to such a transport method of a single-cut sheet associated with an absorbent article, the delivery of the upstream-side end part of each of the single-cut sheets from the first rotating body to the second rotating body can be defined by the adhesive. Thus, it is possible to effectively prevent that the delivery is not properly performed due to a malfunction of the suction operation by the suction holes.

In the transport method of a single-cut sheet associated with an absorbent article, it is preferable that the holding force of the first rotating body occurs due to a suction operation of a plurality of suction holes formed on the outer circumferential surface, and on the outer circumferential surface of the first rotating body, the suction holes are not provided in a portion to which the adhesive of each of the single-cut sheets faces.

According to such a transport method of a single-cut sheet associated with an absorbent article, suction holes are not provided in a portion facing to the adhesive. Thus, it is possible to prevent that the suction holes suck the adhesive and the suction holes are contaminated by the adhesive.

In the transport method of a single-cut sheet associated with an absorbent article, it is preferable that the upstream-side end part of each of the single-cut sheets is bonded by the adhesive to another member associated with manufacture of the absorbent article.

According to such a transport method of a single-cut sheet associated with an absorbent article, the aforementioned adhesive can also be used as adhesive for bonding the upstream-side end part of each of the single-cut sheets to another member. Thus, the adhesive can be effectively used.

Furthermore, disclosed is a transport device of a single-cut sheet associated with an absorbent article, the device enlarging a space between single-cut sheets adjacent in a direction of transport, the single-cut sheets being produced by being sequentially cut from a continuous sheet that is transported in the direction of transport, the device including:

a first transport device that transports the single-cut sheets taking a direction of rotation of a first rotating body as the direction of transport by rotating the first rotating body while holding the single-cut sheets on an outer circumferential surface with a holding force of the outer circumferential surface of the first rotating body, the single-cut sheets being each produced by being cut from the continuous sheet; and a second transport device that transports the single-cut sheets taking a direction of rotation of a second rotating body as the direction of transport by rotating the second rotating body while receiving and holding the single-cut sheets on an outer circumferential surface of the second rotating body, the single-cut sheets being transported from the first rotating body, in the first transport device, an upstream-side end part of each of the single-cut sheets in the direction of transport being bonded to the outer circumferential surface of the first rotating body by adhesive provided at least in a part of the upstream-side end part, each of the single-cut sheets being transported in the direction of transport at a peripheral speed value of the first rotating body, in the second transport device, in a state in which the second rotating body rotates at a peripheral speed value larger than the peripheral speed value of the first rotating body, and the upstream-side end part of each of the single-cut sheets is located on the outer circumferential surface of the first rotating body, the second rotating body transporting each of the single-cut sheets while allowing a portion of each of the single-cut sheets located on the second rotating body to relatively slide behind in the direction of transport with respect to the outer circumferential surface of the second rotating body on the basis that each of the single-cut sheets is transported in the direction of transport at the peripheral speed value of the first rotating body, after the adhesive of the upstream-side end part is separated from the outer circumferential surface of the first rotating body and the upstream-side end part moves from the outer circumferential surface of the first rotating body to the outer circumferential surface of the second rotating body, the second rotating body transporting the single-cut sheets at the peripheral speed value of the second rotating body.

According to such a transport method of a single-cut sheet associated with an absorbent article, effects similar to the case of the above-mentioned manufacturing method can be provided.

First Embodiment

A transport method and transport device of a single-cut sheet of a first embodiment is used, for example, in a manufacturing line of a disposable diaper 1.

Figure 2A:
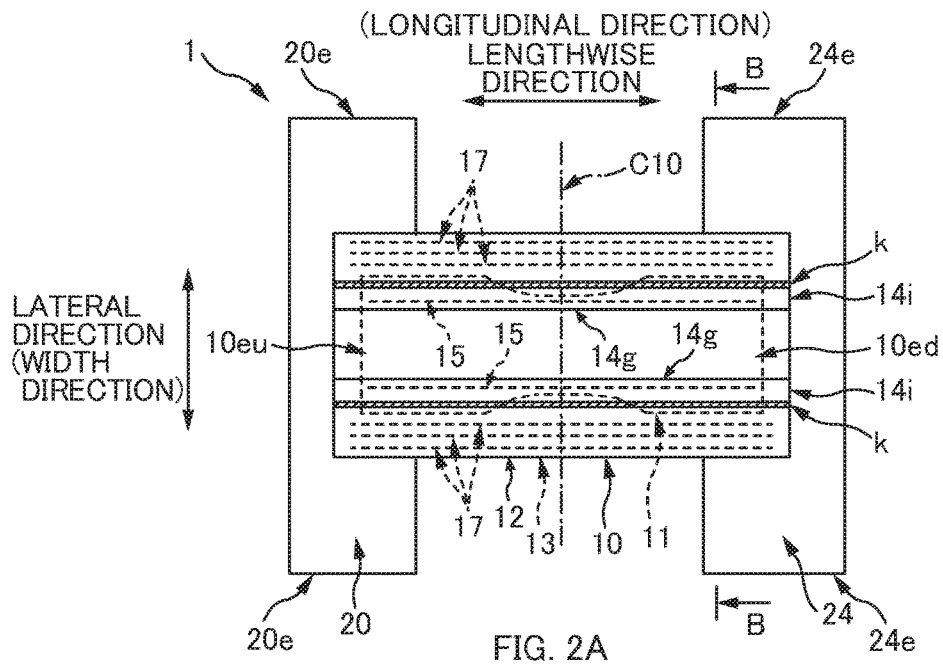
FIG. 2A is a schematic plan view of an open-stated diaper 1 manufactured by a manufacturing apparatus 30 including a transport device of the single-cut sheet of a first embodiment.
Figure 2B:
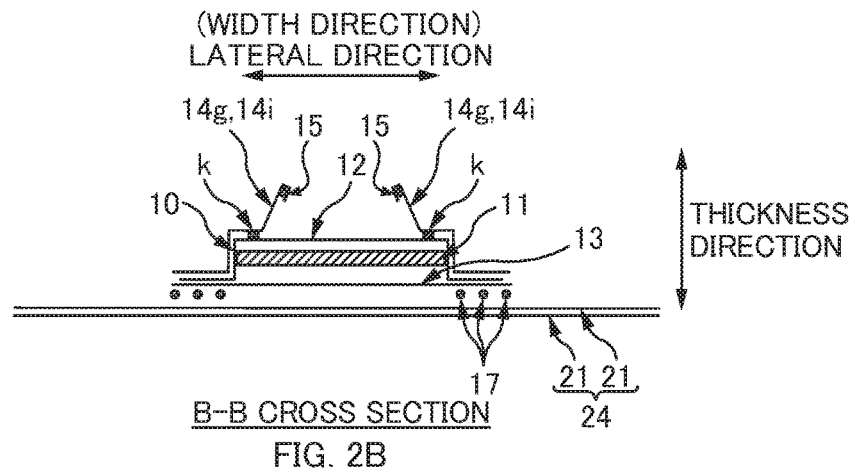
FIG. 2B is a cross-sectional view taken along line B-B in FIG. 2A.
Figure 2C:
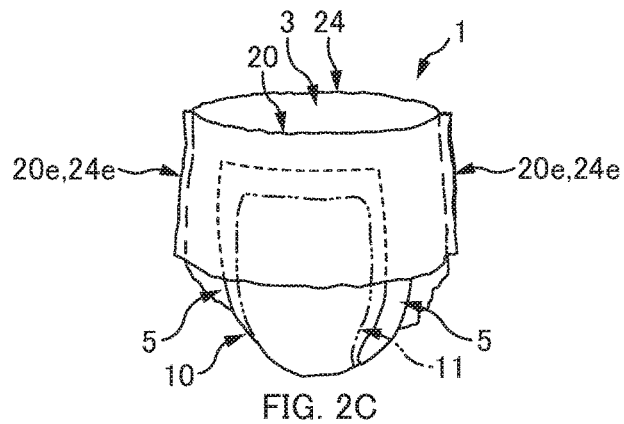
FIG. 2C is a schematic perspective view of the diaper 1 when it is worn.

FIG. 2A to FIG. 2C are explanatory diagrams of the disposable diaper 1. FIG. 2A is a schematic plan view of an open-stated diaper 1, FIG. 2B is a cross-sectional view taken along line B-B in FIG. 2A, and FIG. 2C is a schematic perspective view of the diaper 1 when it is worn.

This diaper 1 includes a lengthwise direction, a lateral direction and a thickness direction as three directions orthogonal to one another in the opened state of FIG. 2A. Further, the diaper 1 is a so-called three-piece type of diaper, and includes a front-side band member 20 that covers a front side portion of a wearer, a back-side band member 24 that covers a back side portion thereof, and an absorbent main body 10 that is applied to the crotch of the wearer and absorbs excrement such urine. In this opened state, the front-side band member 20 and the back-side band member 24 are arranged parallel to each other along the lateral direction with an interval therebetween in the lengthwise direction, the absorbent main body 10 extends between these members, and both end parts 10ed and 10eu of the absorbent main body 10 in the lengthwise direction are joined and fixed to their closest band members 20, 24. This forms the appearance of the diaper 1 into a substantially H shape when viewed in plan view.

Here, from this opened state, the diaper 1 is folded in two taking an approximately center portion C10 in the lengthwise direction of the absorbent main body 10 as a folding position, and the band members 20, 24 opposed to one another in this state folded in two are coupled to one another, for example, by being welded at sites 20e, 24e that should abut against flanks of the wearer. Then, these band members 20, 24 are coupled to one another in an annular shape. This results in the diaper 1 in a wearing state where a waist opening 3 and a pair of leg openings 5, 5 are formed as illustrated in FIG. 2C.

As illustrated in FIG. 2A and FIG. 2B, the absorbent main body 10 has a substantially rectangular shape when viewed in plan view and includes the longitudinal direction, the width direction and the thickness direction orthogonal to one another. In an opened state of FIG. 2A, the longitudinal direction is along the lengthwise direction of the diaper 1. Further, the absorbent main body 10 includes: an absorbent core 11 obtained by forming liquid absorbent material such as pulp fiber and superabsorbent polymer (what is called SAP) into a predetermined shape such as an approximately hourglass shape in plan view; a top sheet 12 that covers the absorbent core 11 from a skin side of the wearer; and a back sheet 13 that covers the absorbent core from a non-skin side. The top sheet 12 is, for example, a fluid-permeable nonwoven fabric having a plane size larger than that of the absorbent core 11. The back sheet 13 is, for example, a fluid-impermeable sheet also having a plane size larger than that of the absorbent core 11. As its example, a fluid-impermeable leak-proof sheet such as polyethylene and a laminated sheet obtained by sticking this leak-proof sheet and an exterior sheet such as a nonwoven fabric (not illustrated) together are included. Then, in a state where these top sheet 12 and back sheet 13 sandwich the absorbent core 11, for example, the top sheet 12 and the back sheet 13 are bonded to one another in a frame shape at parts projecting outside from four sides of the absorbent core 11. This forms the absorbent main body 10. The absorbent core 11 may be coated with a fluid-permeable sheet (not illustrated) such as tissue paper.

As illustrated in FIG. 2B, elastic members 17 such as elastic strings along the lengthwise direction are fixed to parts that project outside of the absorbent core 11 in the lateral direction in the absorbent main body 10, for example, by a hot-melt adhesive in a stretched state in the lengthwise direction. Accordingly, elasticity is imparted to these parts. Here, these parts are parts that will be the leg openings 5 of the diaper 1. Thus, if the stretched state of these parts is released, these parts contract in the lengthwise direction to form a plurality of pleats, and then, these pleats become leg gathers of the respective leg openings 5, 5 of the diaper 1.

Further, in some cases, as in this example, respective end parts in the lateral direction at the top sheet 12 may include barrier cuffs 14g, 14g that stand from a skin side surface of this sheet 12 to prevent side leakage. The respective barrier cuffs 14g are formed by respective barrier cuff sheets 14 fixed to the respective end parts in the lateral direction of the top sheet 12 via fixed portions k. That is, elastic members 15 such as elastic strings are fixed in the stretched state in the lengthwise direction to inside parts 14i with respect to the above-described fixed portions k in the lateral direction in the sheet 14. Then, when this stretched state is released, the inside parts 14i contract in the lengthwise direction, and thus the inside parts 14i stand while forming a plurality of pleats. As a result, the inside parts 14i function as the barrier cuffs 14g. The above-described fixed portions k are formed, for example, by a hot-melt adhesive.

The front-side band member 20 and the back-side band member 24 are both made of a soft sheet material such as nonwoven fabric. Here, as illustrated in FIG. 2B, the respective band members 20, 24 are formed by stacking nonwoven fabrics 21, 21 together. The band members 20, 24 are bonded to respective end parts 10ed, 10eu in the lengthwise direction (longitudinal direction) in the absorbent main body 10. Elastic members (not illustrated) such as elastic strings are fixed to the respective band members 20, 24 in extended states in the lateral direction along this lateral direction. This imparts elasticity in the lateral direction to these band members 20, 24.

Such diaper 1 is manufactured in the manufacturing line. In this line, an intermediate product 1m of the diaper 1 is transported along a predetermined direction of transport. Then, during this transport, various kinds of processes are performed on this intermediate product 1m. Each time the respective processes are performed, a form of the intermediate product 1m is sequentially changed, and finally the diaper 1 as in FIG. 2C is completed. The transport method and the transport device of the single-cut sheet of the first embodiment undertake one of the processes.

Figure 3A:
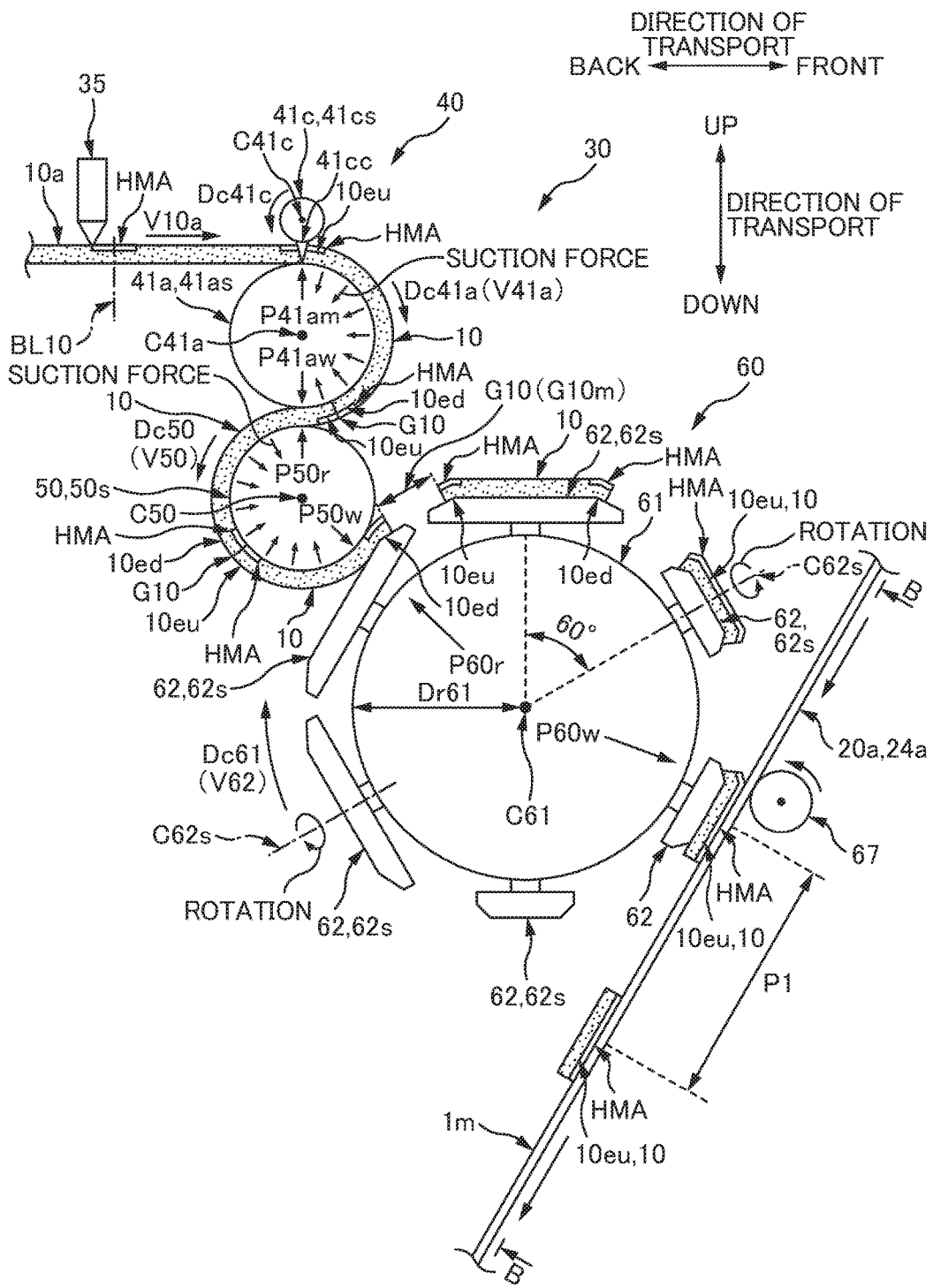
FIG. 3A is a schematic side view of a manufacturing apparatus 30 in which the transport device of the single-cut sheet of the first embodiment is incorporated.
Figure 3B:
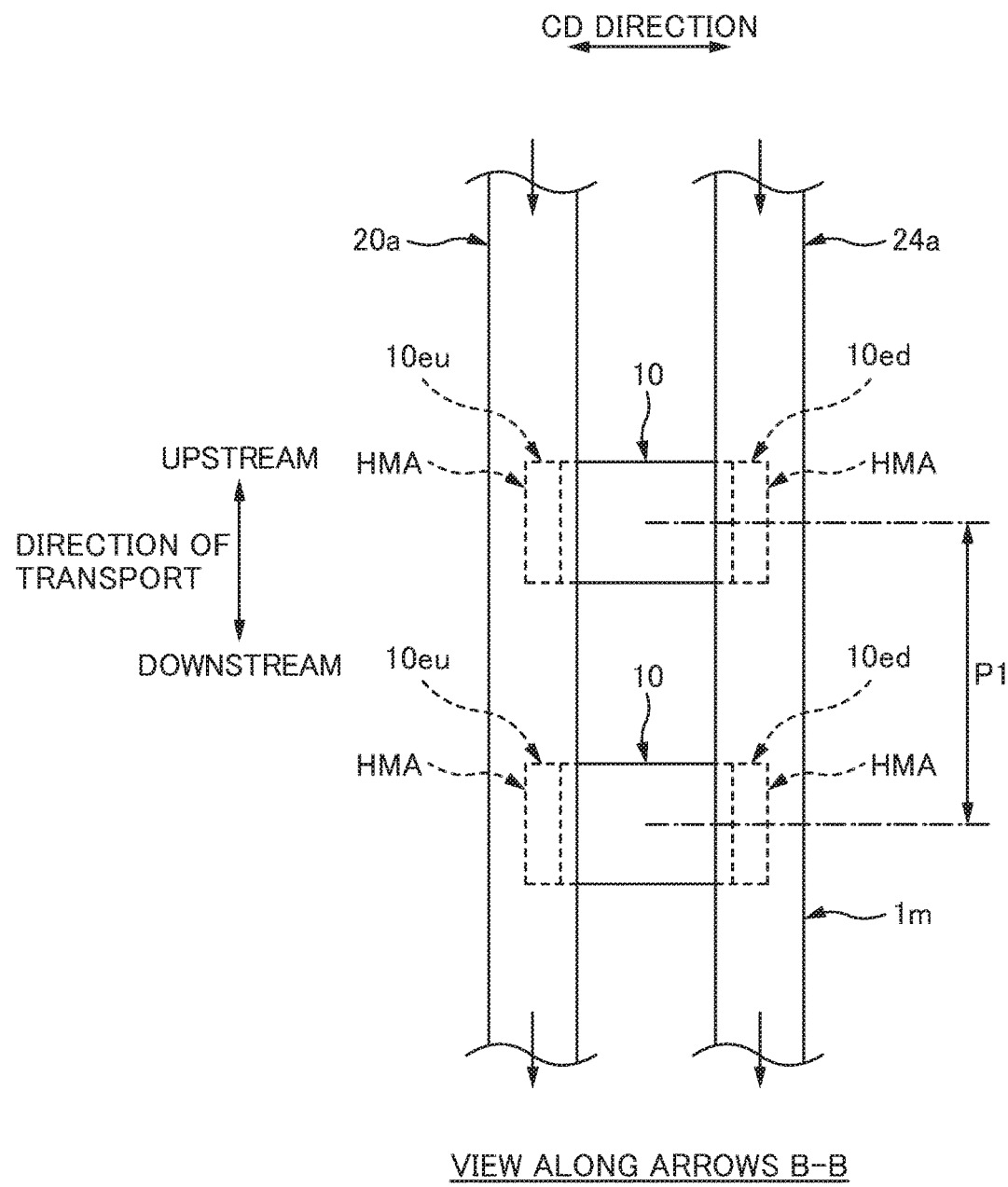
FIG. 3B is a view along arrows B-B in FIG. 3A.

FIG. 3A is a schematic side view of a manufacturing apparatus 30 in which the transport device of the single-cut sheet of the first embodiment is incorporated. FIG. 3B is a view along arrows B-B in FIG. 3A.

In the following, a width direction of the manufacturing line is also referred to as a "CD direction". Further, in this example, this CD direction is along the horizontal direction. In this manufacturing line, the intermediate product 1m of the diaper 1 is transported taking any direction in a planar surface perpendicular to the CD direction as the direction of transport. That is, the direction of transport is directed to a direction defined by both a vertical up-down direction and a horizontal front-back direction.

As illustrated in FIG. 3A, a continuous body 10a of the absorbent main body is transported to this manufacturing apparatus 30, the continuous body 10a being formed by connecting a plurality of absorbent main bodies 10, 10 . . . in the lengthwise direction (longitudinal direction) from the upstream step. That is, the top sheet 12, the back sheet 13, and a pair of barrier cuff sheets 14, 14, which constitute the absorbent main body 10, are each in a state of a continuous sheet that is continuous in the direction of transport. Then, the absorbent cores 11, 11 . . . interposed between the respective continuous sheets of these top sheet 12 and back sheet 13 are in a state aligned with an interval between the absorbent cores 11 adjacent to one another in the direction of transport. Each of the continuous sheets is in a state of being mutually integrally bonded to the continuous sheet mutually adjacent in the thickness direction or the absorbent core 11 by adhesion or the like.

Also, a pair of band members 20 and 24 is transported from another upstream step taking the continuous direction of the continuous bodies 20a, 24a as a direction of transport in the form of continuous bodies 20a, 24a along the direction of transport and in a state of being arranged parallel to each other with an interval between each other in the CD direction.

In the manufacturing apparatus 30, first, a single-cut absorbent main body 10 (corresponding to a single-cut sheet) in which the longitudinal direction thereof is along the direction of transport is produced by being cut from the continuous body 10a (corresponding to a continuous sheet) of the absorbent main body. Next, the longitudinal direction of the produced absorbent main body 10 is changed from the direction of transport to the CD direction. Then, the absorbent main body 10 in which the longitudinal direction thereof is along the CD direction is extended across and bonded to a pair of band-member continuous bodies 20a, 24a, at a product pitch P1 in the direction of transport. Accordingly, an approximately ladder-type member 1m as in FIG. 3B is manufactured as the intermediate product 1m of the diaper 1.

The manufacturing apparatus 30 includes: an adhesive applying device 35 that applies adhesive HMA to the continuous body 10a of the absorbent main body to be transported from the upstream step along the direction of transport; a cutter device 40 that cuts the continuous body 10a of the absorbent main body to produce the absorbent main body 10; a delivering roll 50 that receives the absorbent main body 10 that is to be transported from the cutter device 40 on an outer circumferential surface 50s; and a rotating drum device 60 that changes the longitudinal direction of the absorbent main body 10 received from the delivering roll 50 from the direction of transport to the CD direction and allows the absorbent main body 10 whose longitudinal direction is along the CD direction to be extended across the pair of band-member continuous bodies 20a, 24a and to be bonded thereto.

The adhesive applying device 35 applies the adhesive HMA such as a hot-melt adhesive so as to straddle a boundary position BL10 between the adjacent absorbent main bodies 10, 10 in the direction of transport in the continuous body 10a of the absorbent main body. Accordingly, in a state of the single-cut absorbent main body 10 produced by being cut by the cutter device 40 after that, the adhesive HMA is applied to respective end parts 10eu, 10ed in the longitudinal direction. The adhesive HMA of these end parts 10eu, 10ed is basically used for bonding with the pair of continuous bodies 20a, 24a (corresponding to another member) of the band-shaped members. As an application pattern of the adhesive HMA, a Ω pattern in which a plurality of wavy lines along the direction of transport is arranged in CD direction, a stripe pattern in which a plurality of straight lines along the direction of transport is arranged in the CD direction, a solid-coating pattern in which the adhesive is applied without any space in the application target area can be exemplified. In the present embodiment, Ω pattern is used. Also, in this example, although the adhesive HMA is applied to approximately over the entire area in the CD direction, the invention is not limited thereto.

The cutter device 40 includes a cutter roll 41c (corresponding to a fourth rotating body) and an anvil roll 41a (corresponding to a third rotating body) whose respective outer circumferential surfaces 41cs, 41as are faced and which are rotatably supported around rotation shafts C41c and C41a along the CD direction, respectively. The cutter roll 41c and the anvil roll 41a are driven to rotate by a servomotor (not shown) as a driving source. The cutter roll 41c includes a blade-shaped cutter blade 41cc extending in the CD direction while protruding from the outer circumferential surface 41cs at a pitch corresponding to a length in the longitudinal direction of the absorbent main body 10 in the direction of rotation Dc41c. The anvil roll 41a is driven to rotate so as to be the same peripheral speed value V41a (m/s) as the transport speed V10a (m/s) of the continuous body 10a while holding the continuous body 10a of the absorbent main body on the outer circumferential surface 41as by a suction force of the outer circumferential surface 41as, the continuous body 10a of the absorbent main body being transported from the upstream step. Thus, the continuous body 10a of the absorbent main body is transported taking the direction of rotation Dc41a as a direction of transport. Further, the cutter roll 41c rotates along the direction of transport so that the cutter blade 41cc faces the aforementioned boundary position BL10 in the continuous body 10a of the absorbent main body every time the boundary position BL10 passes by the position of the cutter roll 41c. Accordingly, every time of this passing, the cutter blade 41cc faces the outer circumferential surface 41as of the anvil roll 41a, and at that time, the outer circumferential surface 41as functions as a surface-like receiving blade that receives the cutter blade 41cc. Consequently, the continuous body 10a of the absorbent main body is cut at the boundary position BL10. As a result, a single-cut absorbent main body 10 is produced on the outer circumferential surface 41as of the anvil roll 41a, and the absorbent main body 10 is transported taking the direction of rotation Dc41a as the direction of transport while being held on the outer circumferential surface 41as of the anvil roll 41a by the suction force, thus being delivered to the delivering roll 50 at a delivering position P41aw set at a predetermined position in the direction of rotation Dc41a.

The suction force of the outer circumferential surface 41as of the anvil roll 41a occurs in a rotation range from a winding start position P41am, at which the continuous body 10a of the absorbent main body starts to wind in the direction of rotation Dc41a of the anvil roll 41a, to a slightly upstream position of the aforementioned delivering position P41aw. However, the suction force does not occur in a rotation range from the delivering position P41aw to a slightly upstream position of the aforementioned winding start position P41am. Thus, when each portion of the absorbent main body 10 passes by the delivering position P41aw, the each portion can smoothly leave the outer circumferential surface 41as of the anvil roll 41a. Consequently, the anvil roll 41a can deliver the absorbent main body 10 promptly to the delivering roll 50.

The delivering roll 50 (corresponding to a first rotating body) is also rotatably supported about a rotation shaft C50 along the CD direction. The delivering roll 50 is driven to rotate by a servomotor (not shown) as a driving source. Further, the outer circumferential surface 50s of this delivering roll 50 is also configured to be able to generate suction force (corresponding to holding force). In this example, a plurality of suction holes 50h, 50h . . . (see FIG. 6A) is discretely formed on the outer circumferential surface 50s, and thus the outer circumferential surface 50s generates the suction force due to suction operation of these suction holes 50h, 50h . . . . Furthermore, the outer circumferential surface 50s of the delivering roll 50 faces the outer circumferential surface 41as of the anvil roll 41a while being closest thereto at the aforementioned delivering position P41aw, so that a position P50r corresponding to the aforementioned delivering position P41aw in the direction of rotation Dc50 of the delivering roll 50 is a receiving position P50r at which the delivering roll 50 receives the absorbent main body 10 from the anvil roll 41a.

Accordingly, when each portion of the absorbent main body 10 passes by the aforementioned delivering position P41aw of the anvil roll 41a, the each portion is sequentially sucked and held on the outer circumferential surface 50s by the suction force of the outer circumferential surface 50s of the delivering roll 50. Thereby, the absorbent main body 10 is delivered from the outer circumferential surface 41as of the anvil roll 41a to the outer circumferential surface 50s of the delivering roll 50. Then, the delivering roll 50 holds the received absorbent main body 10 by the suction force of the outer circumferential surface 50s, transports the absorbent main body 10 taking the direction of rotation Dc50 of the delivering roll 50 as the direction of transport with its rotation, and delivers the absorbent main body 10 to the rotating drum device 60 at the delivering position P50w in the direction of rotation Dc50.

Note that, the peripheral speed value V50 (m/s) of the outer circumferential surface 50s of the delivering roll 50 is also controlled so as to be equal to the aforementioned transport speed V10a (m/s). Thus, between the absorbent main bodies 10, 10 arranged in the direction of transport, a state where there is substantially no space G10 is maintained.

Moreover, the suction force of the outer circumferential surface 50s of the delivering roll 50 occurs in a rotation range from the aforementioned receiving position P50r in the direction of rotation Dc50 of the delivering roll 50 to the slightly upstream position of the aforementioned delivering position P50w. However, the suction force does not occur in a rotation range from the delivering position P50w to the slightly upstream position of the aforementioned receiving position P50r. Thus, when each portion of the absorbent main body 10 passes by the delivering position P50w, the each portion can smoothly leave the outer circumferential surface 50s of the delivering roll 50. Consequently, the delivering roll 50 can deliver the absorbent main body 10 promptly to the rotating drum device 60.

The rotating drum device 60 includes a rotating drum 61 (corresponding to a second rotating body). The rotating drum 61 is driven to rotate around a rotation shaft C61 along the CD direction. As a driving source for drive rotation, for example, a servomotor (not shown) is used. Further, on the outer periphery of the rotating drum 61, six holding pads 62, 62 . . . are arranged at every 60 degrees as one example of the predetermined degrees in a direction of rotation Dc61, as one example of the plurality of holding pads. Then, the plurality of holding pads 62, 62 . . . rotates in the direction of rotation DC61 together with the rotating drum 61, and thus the plurality of holding pads 62, 62 . . . circulates along circulating trajectory Tr in one direction (in a clockwise direction in the example of FIG. 3A) about the aforementioned rotation shaft C61.

Each of the holding pads 62 includes a holding surface 62s (corresponding to an outer circumferential surface of the second rotating body) that generates suction force, and the holding surface 62s faces outside a direction of rotational radius Dr61 of the rotating drum 61. Further, the aforementioned outer circumferential surface 50s of the delivering roll 50 faces a receiving position P60r set on the circulating trajectory Tr while being closest thereto. That is, the aforementioned delivering position P50w set in the aforementioned direction of rotation Dc50 of the delivering roll 50 faces the receiving position P60r. Furthermore, the rotating operation of the rotating drum 61 is controlled based on a synchronization signal for synchronizing the rotating operation with a cutting operation of the cutter device 40. This allows each holding pad 62 to pass by the receiving position P60r in accordance with each absorbent main body 10 arranged on the delivering roll 50 in the direction of transport. That is, each of the holding pads 62 passes by the receiving position P60r so as to correspond to each of the absorbent main bodies 10 in one-to-one correspondence.

Accordingly, when each portion of the absorbent main body 10 passes by the delivering position P50w of the delivering roll 50, the each portion is sequentially sucked and held on the holding surface 62s by the suction force of the holding surface 62s of the corresponding holding pad 62, and thus, the absorbent main body 10 is delivered from the outer circumferential surface 50s of the delivering roll 50 to the holding surface 62s of the holding pad 62.

Then, the each holding pad 62 moves to a delivering position P60w on the downstream side in the circulating trajectory Tr while holding the absorbent main body 10 on the holding surface 62s as it is. Here, in the process in which the holding pad 62 moves to the delivering position P60w, the holding pad 62 rotates around an approximately plane center C62s of the holding surface 62s only by 90 degrees. Thus, the absorbent main body 10 on the holding surface 62s also rotates around the approximately plane center C62s only by 90 degrees. As a result, the longitudinal direction of the absorbent main body 10 is changed from the direction of transport to the CD direction. Thereby, the absorbent main body 10 becomes a posture configured to be extended across the pair of band-member continuous bodies 20a, 24a.

FIGS. 4A to 4C are explanatory diagrams of the holding surface 62 of the holding pad 62. FIG. 4A is a schematic plan view when the holding pad 62 is seen from the holding surface 62s side, FIG. 4B is a view along arrows B-B in FIG. 4A, and FIG. 4C is a view along arrows C-C in FIG. 4A.

As illustrated in FIG. 4A, the holding surface 62s of the holding pad 62 includes the longitudinal direction and the width direction so as to correspond to the planar shape of the absorbent main body 10 in order to ensure holding of the absorbent main body 10 from end to end. Specifically, the holding surface 62s includes a flat plane region 62sp having a rectangular shape when viewed in plan view along the aforementioned longitudinal direction and the width direction at a center side position in the longitudinal direction and a center side position in the width direction. Then, at the receiving position P60r, the longitudinal direction of the holding surface 62s is set along the direction of transport, and thus the absorbent main body 10 can be held by the holding surface 62s over the entire length of the absorbent main body 10 in the longitudinal direction.

In this example, each holding surface 62s has inclined regions 62st1, 62st1, 62st2 and 62st2 which are inclined from the plane region 62sp and are respectively adjacent to the four sides of the aforementioned plane region 62sp of the holding surface 62s. Accordingly, the shape of the holding pad 62 when seen from the width direction is a substantially equilateral trapezoidal shape such that the center portion in the longitudinal direction projects outward in the direction of rotational radius Dr61 compared with both end parts as illustrated in FIG. 4B. Also, the shape of the holding pad 62 when seen from the longitudinal direction is a substantially equilateral trapezoidal shape such that the center portion in the width direction projects outward in the direction of rotational radius Dr61 compared with both end parts as illustrated in FIG. 4C. Thus, at the receiving position P60r where the longitudinal direction of the holding surface 62s is set along the direction of transport, the holding surface 62s can smoothly receive the absorbent main body 10 based on the former equilateral trapezoidal shape, whereas, at the delivering position P60w where the width direction of the holding surface 62s is set along the direction of transport, the holding surface 62s can smoothly deliver the absorbent main body 10 based on the latter substantially equilateral trapezoidal shape.

Note that, the suction force of the holding surface 62s occurs at least in the rotation range from the receiving position P60r on the circulating trajectory Tr (the direction of rotation DC61 of the rotating drum 61) to the slightly upstream position of the delivering position P60w (FIG. 3A). Thus, when the holding pad 62 passes by the receiving position P60r, the holding pad 62 can promptly receive the absorbent main body 10 by the suction force of the holding surface 62s. The occurrence of such suction force is made by a suction operation of a plurality of suction holes 62h, 62h . . . discretely formed on the holding surface 62s as illustrated in FIG. 4A to FIG. 4C. That is, each suction hole 62h is communicated with a pressure chamber SP62 in the holding pad 62, and this pressure chamber SP62 is communicated with a negative pressure source such as a compressor or blower in a rotation range at least from the receiving position P60r to the slightly upstream position of the delivering position P60w. Thus, in the holding pad 62d moving in this rotation range, each suction hole 62h performs the suction operation, and accordingly, the suction force occurs on the holding surface 62s of the holding pad 62.

Meanwhile, as illustrated in FIGS. 3A and 3B, a transport roller 67 that guides travel of the pair of band-member continuous bodies 20a, 24a is disposed at the delivering position P60w on the circulating trajectory Tr of the holding pad 62. When the holding pad 62 passes by the delivering position P60w, the transport roller 67 presses the pair of band-member continuous bodies 20a, 24a against the absorbent main body 10 held by the holding pad 62. This bonds the respective end parts 10ed, 10eu to the pair of continuous bodies 20a, 24a of the band members 20 and 24a by the adhesive HMA of the respective end parts 10ed, 10eu in the CD direction of the absorbent main body 10. Thereby, the absorbent main body 10 is delivered from the holding pad 62 to the pair of band-member continuous bodies 20a, 24a, thus producing an approximately ladder-shaped intermediate product 1m as in FIG. 3B. That is, the approximately ladder-shaped intermediate product 1m is produced in such a manner that the plurality of absorbent main bodies 10, 10 . . . is arranged in the direction of transport and is bonded on the pair of band-member continuous bodies 20a, 24a.

Meanwhile, as illustrated in FIG. 3A, the absorbent main body 10 immediately after being cut from the continuous body 10a of the absorbent main body by the cutter device 40 is in a state of substantially abutting against another absorbent main body 10 located downstream in the direction of transport. In other words, these absorbent main bodies 10, 10 are arranged in the direction of transport in a state where there is substantially no space G10 between each other. Then, in this state where there is substantially no space G10, a pitch P10 in which the absorbent main bodies 10, 10 are arranged in the direction of transport is made smaller than a product pitch P1 (FIG. 3A and FIG. 3B) in the direction of transport in which each absorbent main body 10 is to be extended across the pair of band-member continuous bodies 20a, 24a.

Thus, in this manufacturing apparatus 30, the aforementioned arrangement pitch P10 is enlarged to the product pitch P1 between the delivering roll 50 and the rotating drum device 60. This enlarges the space G10 between the absorbent main bodies 10, 10 from approximately zero to a target value G10m (FIG. 3A).

Here, this enlargement process is realized as follows. First, the peripheral speed value V62 in the direction of rotation Dc61 of the holding surface 62s of the holding pad 62 of the rotating drum 61 is made larger than the peripheral speed value V50 in the direction of rotation Dc50 of the outer circumferential surface 50s of the delivering roll 50. Note that, this increase of the peripheral speed value V62 can be realized, for example, by moving the position of the holding surface 62 of the holding pad 62 in the direction of rotational radius Dr61 outward to fix it at that position in advance, and thus by adjusting the size of the turning radius around the rotation shaft C61 of the holding surface 62s. Also, as described above, the delivering roll 50 substantially relatively immovably sucks and holds the absorbent main body 10 on the outer circumferential surface 50s.

Thus, basically, as long as the upstream-side end part 10eu of the absorbent main body 10 in the direction of transport is located on the outer circumferential surface 50s of the delivering roll 50, the absorbent main body 10 is transported at the peripheral speed value V50 of the outer circumferential surface 50s of the delivering roll 50. Accordingly, the holding pad 62 of the rotating drum 61 transports a portion of the absorbent main body 10, which is located on the holding surface 62s of the holding pad 62, while allowing the portion to relatively slide behind in a direction of transport with respect to the holding surface 62s.

On the other hand, after the upstream-side end part 10eu of the absorbent main body 10 in the direction of transport is transferred from the outer circumferential surface 50s of the delivering roll 50 to the holding surface 62s of the holding pad 62 of the rotating drum 61, the holding pad 62 transports the absorbent main body 10 in the direction of rotation Dc61 at the large peripheral speed value V62 of the holding pad 62. Accordingly, the space G10 between this absorbent main body 10 and the absorbent main body 10 which is adjacent on the upstream side and is produced by being cut is enlarged up to the aforementioned target value G10m from approximately zero.

However, when the suction force of the outer circumferential surface 50s of the delivering roll 50 is insufficient, the suction force may yield to a sliding force F (FIG. 5) directed to the downstream side, which is imparted from the holding surface 62s of the holding pad 62 of the rotating drum 61 to the absorbent main body 10. In that case, the absorbent main body 10 slides to the downstream side on the outer circumferential surface 50s of the delivering roll 50 which should originally hold the absorbent main body 10 in a relatively immovable manner. Consequently, the absorbent main body 10 is shifted to the downstream side in the direction of transport from the position where it should be originally located. Then, the space G10 between this absorbent main body 10 and the absorbent main body 10 located on the downstream side becomes smaller than the aforementioned target value G10m. That is, the enlargement of the space G10 becomes insufficient. This may result in the deterioration of accuracy in the bonding process to be carried out afterward at the delivering position P60w.

In this first embodiment, as illustrated in FIG. 3A, the adhesive HMA is provided to each of the end parts 10ed, 10eu of the absorbent main body 10 in the direction of transport, and thus each of the end parts 10ed, 10eu is bonded to the outer circumferential surface 50s of the delivering roll 50 with the adhesive HMA. Accordingly, in addition to the suction force of the outer circumferential surface 50s of the delivering roll 50, the absorbent main body 10 is held on the outer circumferential surface 50s of the delivering roll 50 also by the adhesive strength of the adhesive HMA of the aforementioned end parts 10ed, 10eu.

Thus, when the upstream-side end part 10eu of the absorbent main body 10 in the direction of transport is located on the outer circumferential surface 50s of the delivering roll 50, the absorbent main body 10 can be certainly held on the outer circumferential surface 50s, thereby enabling the absorbent main body 10 to be certainly transported at the peripheral speed value V50 of the outer circumferential surface 50s of the delivering roll 50. As a result, it is possible to allow a portion of the absorbent main body 10 which is located on the holding pad 62 of the rotating drum 61 to certainly relatively slide behind in the direction of transport with respect to the holding surface 62s of the holding pad 62, and thus, the space G10 between this absorbent main body 10 and the adjacent absorbent main body 10 on the downstream side thereof, that is, the absorbent main body 10 being transported at the large peripheral speed value V50 of the holding pad 62, can be reliably enlarged.

Incidentally, the adhesive HMA of each of the end parts 10ed, 10eu of the aforementioned absorbent main body 10 is formed by applying the adhesive HMA to the continuous body 10a of the absorbent main body by the aforementioned adhesive applying device 35. Thus, when the holding pad 62 holding the absorbent main body 10 passes by the delivering position P60w, the applied adhesive HMA is used for bonding the absorbent main body 10 and the pair of band-member continuous bodies 20a, 24a.

Further, in this example, as illustrated in FIG. 3A, the adhesive applying device 35 applies the adhesive HMA so as to include the aforementioned boundary position BL10 in the continuous body 10a of the absorbent main body. Then, the cutter device 40 cuts the continuous body 10a of the absorbent main body using the boundary position BL10 as a cutting position. In this example, not only can the adhesive HMA be provided to each of the upstream-side end part 10eu and the downstream-side end part 10ed of the absorbent main body 10 in the direction of transport as described above, but also the adhesive HMA can be provided to the most upstream part 10eue (FIG. 5) of the absorbent main body 10 in the direction of transport. Consequently, the adhesive strength due to such adhesive HMA can be certainly imparted over substantially the entire period during which the absorbent main body 10 is held by the delivering roll 50.

Further, in this example, as illustrated in FIG. 3A, the adhesive HMA is applied to one of two surfaces of the continuous body 10a of the absorbent main body, the one facing toward the outer circumferential surface 41cs of the cutter roll 41c. Thus, adhesive soiling of the adhesive HMA which may occur in the cutter device 40 can be easily cleaned. In other words, when the adhesive HMA adheres to a surface-like receiving blade such as an outer circumferential surface 41as of the anvil roll 41a, the adhesive HMA is less likely to be cleaned; however, in this example, the adhesive HMA of the continuous body 10a of the absorbent main body is directed toward the cutter blade 41cc of the cutter roll 41c, thereby allowing the adhesive HMA to exclusively adhere to the cutter blade 41cc. Since this cutter blade 41cc has a blade shape protruding from the outer circumferential surface 41cs, the adhesive soiling of the adhesive HMA can be relatively easily removed, for example, by applying a sponge-like member impregnated with a cleaning liquid. As a result, it is easier to clean the cutter device 40 in general. Further, in this example, the absorbent main body 10 is transported to the delivering roll 50 via the anvil roll 41a. Accordingly, as described above, if the adhesive HMA is applied to one of two surfaces of the continuous body 10a of the absorbent main body, the one facing toward the outer circumferential surface 41cs of the cutter roll 41c, the surface to which the adhesive HMA has been applied in the absorbent main body 10 can be directed to the outer circumferential surface 50s of the delivering roll 50. Consequently, it is possible to allow the adhesive HMA to reliably contribute to the holding of the absorbent main body 10 on the outer circumferential surface 50s of the delivering roll 50.

Figure 5:
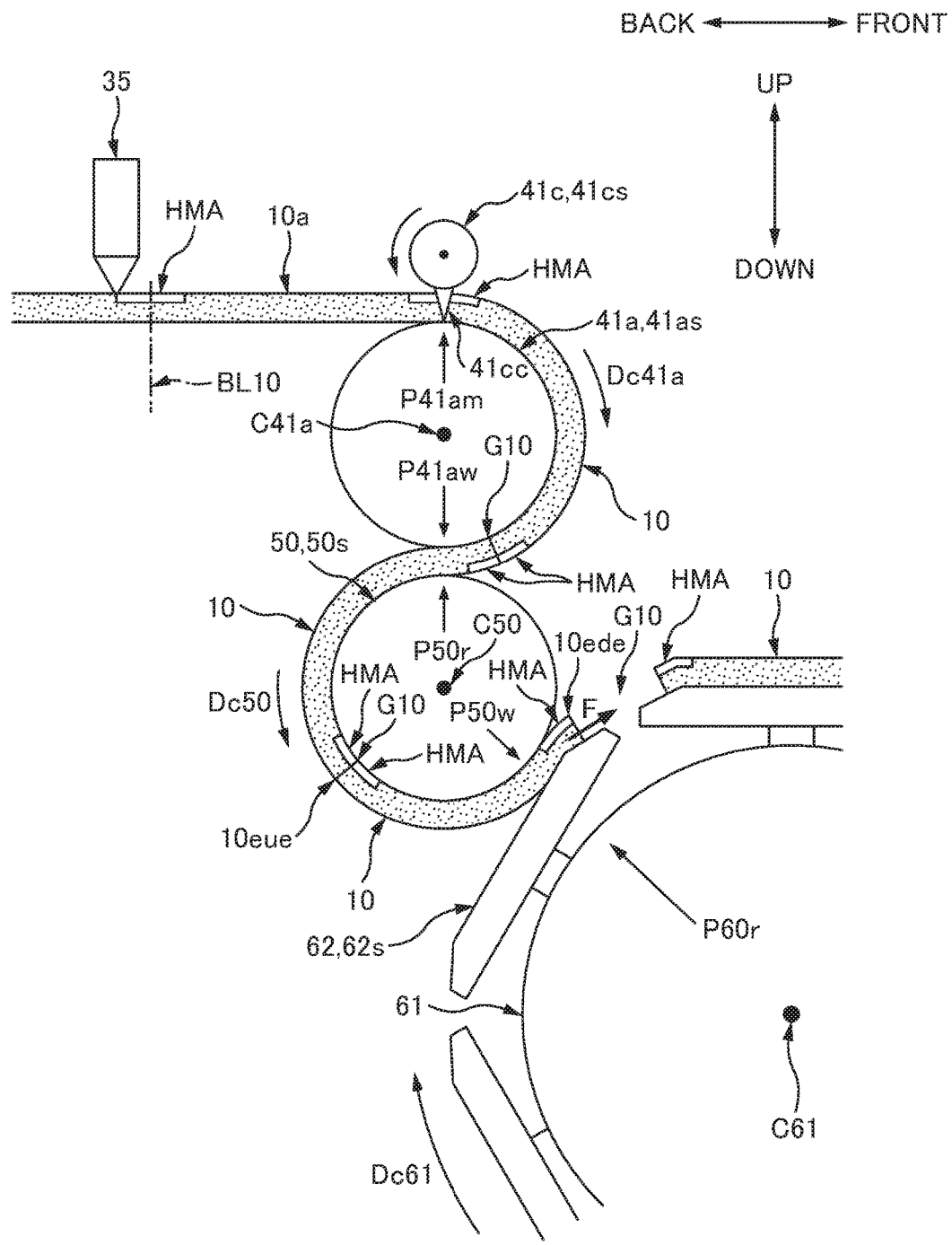
FIG. 5 is a schematic side view illustrating a part of the manufacturing apparatus 30 in an enlargement manner.

In this example, moreover, the following matter has been realized based on the position adjustment of the receiving position P50r and the delivering position P50w in the direction of rotation Dc50 of the delivering roll 50 (see FIG. 5). That is, after the most upstream part 10eue of the absorbent main body 10 in the direction of transport moves from the anvil roll 41a to the delivering roll 50, the most downstream part 10ede of the absorbent main body 10 in the direction of transport moves from the delivering roll 50 to the holding pad 62 of the rotating drum 61.

Thus, when the absorbent main body 10 moves from the delivering roll 50 to the holding pad 62 of the rotating drum 61, it is possible to allow the absorbent main body 10 not to straddle both the delivering roll 50 and the anvil roll 41a. In this way, the absorbent main body 10 can be transported to the holding pad 62 of the rotating drum 61 exclusively based on only the rotating operation of the delivering roll 50. Accordingly, it can be prevented that the rotating operation of the anvil roll 41a becomes a disturbance and thus accuracy of movement of the absorbent main body 10 to the holding pad 62 of the rotating drum 61 is deteriorated.

From the viewpoint of reliably realizing the above-mentioned points, the circumference length of the outer circumferential surface 50s of the delivering roll 50 is preferably made longer than the length of the absorbent main body 10 in the direction of transport (longitudinal direction), and further preferably, the circumference length may be made twice or more the aforementioned length of the absorbent main body 10. For example, the circumference length may be an integral (excluding 1) multiple of the length of the absorbent main body 10.

Figure 6:
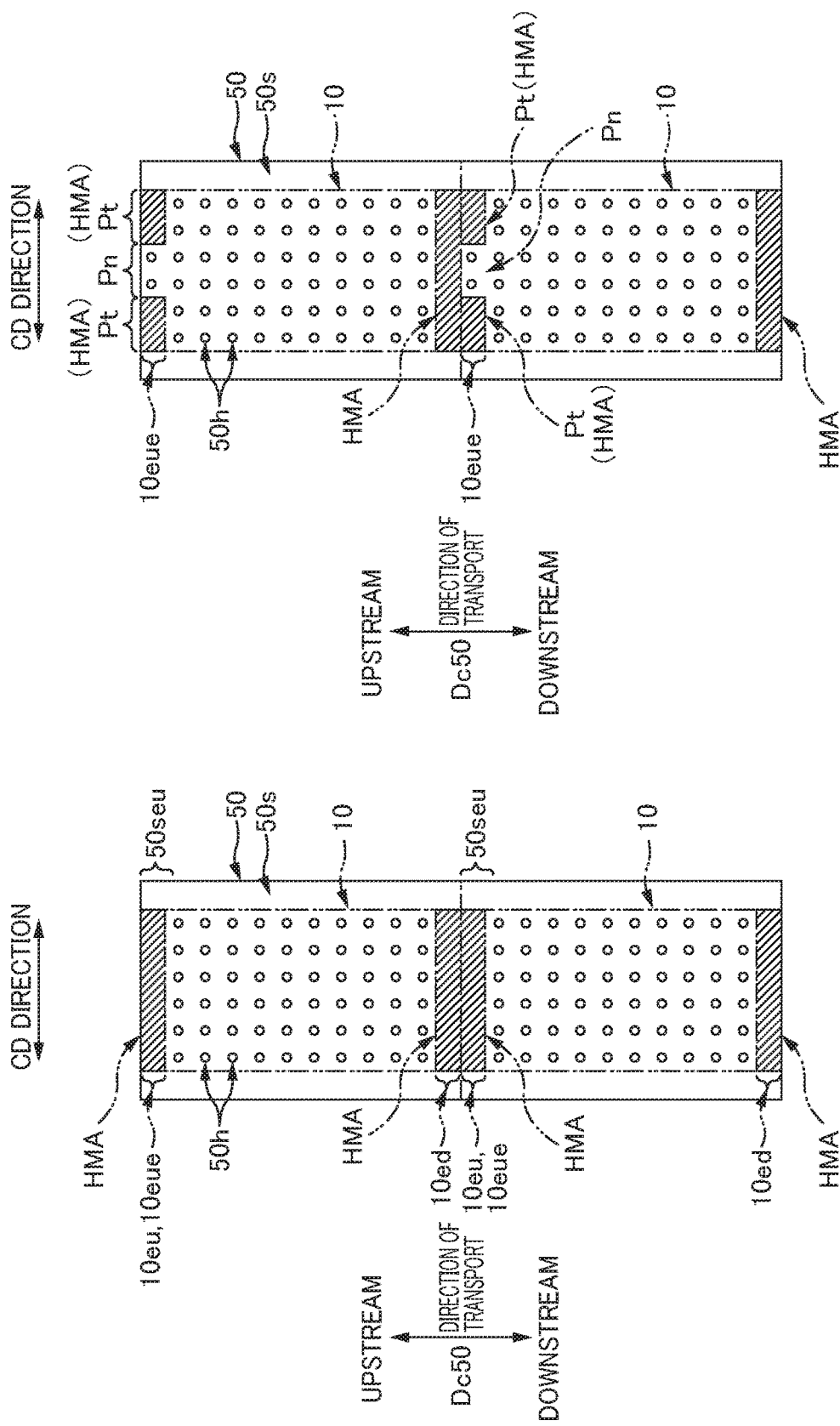
FIG. 6A and FIG. 6B are explanatory diagrams of arrangement examples of suction holes 50h, 50h . . . on an outer circumferential surface 50s of a delivering roll 50, and are schematic views each illustrating the outer circumferential surface 50s developed in a direction of rotation Dc50.

FIG. 6A and FIG. 6B are explanatory diagrams of arrangement examples of the suction holes 50h, 50h . . . on the outer circumferential surface 50s of the delivering roll 50, and are schematic views illustrating the outer circumferential surface 50s so as to be developed in the direction of rotation Dc50. In the examples of these FIG. 6A and FIG. 6B, the circumference length of the outer circumferential surface 50s of the delivering roll 50 is made twice the length of the absorbent main body 10 in the longitudinal direction. Further, in FIG. 6A and FIG. 6B, in order to recognize a portion where the absorbent main body 10 and the adhesive HMA face the outer circumferential surface 50s of the delivering roll 50, the absorbent main body 10 and the adhesive HMA are also virtually illustrated together by double-dotted chained lines, and the adhesive HMA is illustrated by further giving hatchings to each adhesive HMA.

In the example of FIG. 6A, a plurality of suction holes 50h, 50h . . . is discretely disposed on the outer circumferential surface 50s of the delivering roll 50 in both the direction of rotation Dc50 and the CD direction. However, in a part 50seu of the outer circumferential surface 50s to which the upstream-side end part 10eu of the absorbent main body 10 faces, the suction holes 50h, 50h . . . are not provided on the upstream side of a portion facing to the adhesive HMA. Thus, the delivery of the upstream-side end part 10eu of the absorbent main body 10 from the delivering roll 50 to the holding pad 62 of the rotating drum 61 can be defined by the adhesive HMA. Consequently, it is possible to effectively prevent that the delivery is not properly performed due to a malfunction of the suction operation by the suction holes 50h.

In this example of FIG. 6A, the adhesive HMA is applied to the most upstream part 10eue of the absorbent main body 10 over the entire region thereof, whereas no suction holes 50h, 50h . . . are provided in this most upstream part 10eue. However, the suction holes may be provided as shown in the example of FIG. 6B in some cases. That is, the most upstream part 10eue of the absorbent main body 10 in the direction of transport may include an applied portion Pt where the adhesive HMA is applied and a non-applied portion Pn where the adhesive HMA is not applied alternately in the CD direction, the suction hole 50h may not be provided at a portion facing to the aforementioned applied portion Pt, and the suction hole 50h may be provided at a portion facing to the non-applied portion Pn on the outer circumferential surface 50s of the delivering roll 50. Also in this case, the delivery of the upstream-side end part 10eu of the absorbent main body 10 can be defined by the adhesive HMA in a similar manner as mentioned above.

Furthermore, in these examples of FIG. 6A and FIG. 6B, the suction holes 50h, 50h . . . are not provided on the outer circumferential surface 50s of the delivering roll 50 in portions to which the adhesive HMA of the absorbent main body 10 faces. By having such a constitution, it is possible to prevent that the suction holes 50h suck the adhesive HMA and are contaminated by the adhesive HMA. However, the invention is not limited thereto. That is, when such a contamination does not become a big problem, the suction holes 50h may be provided on the outer circumferential surface 50s of the delivering roll 50 in portions to which the adhesive HMA of the absorbent main body 10 faces.

Second Embodiment

Figure 7:
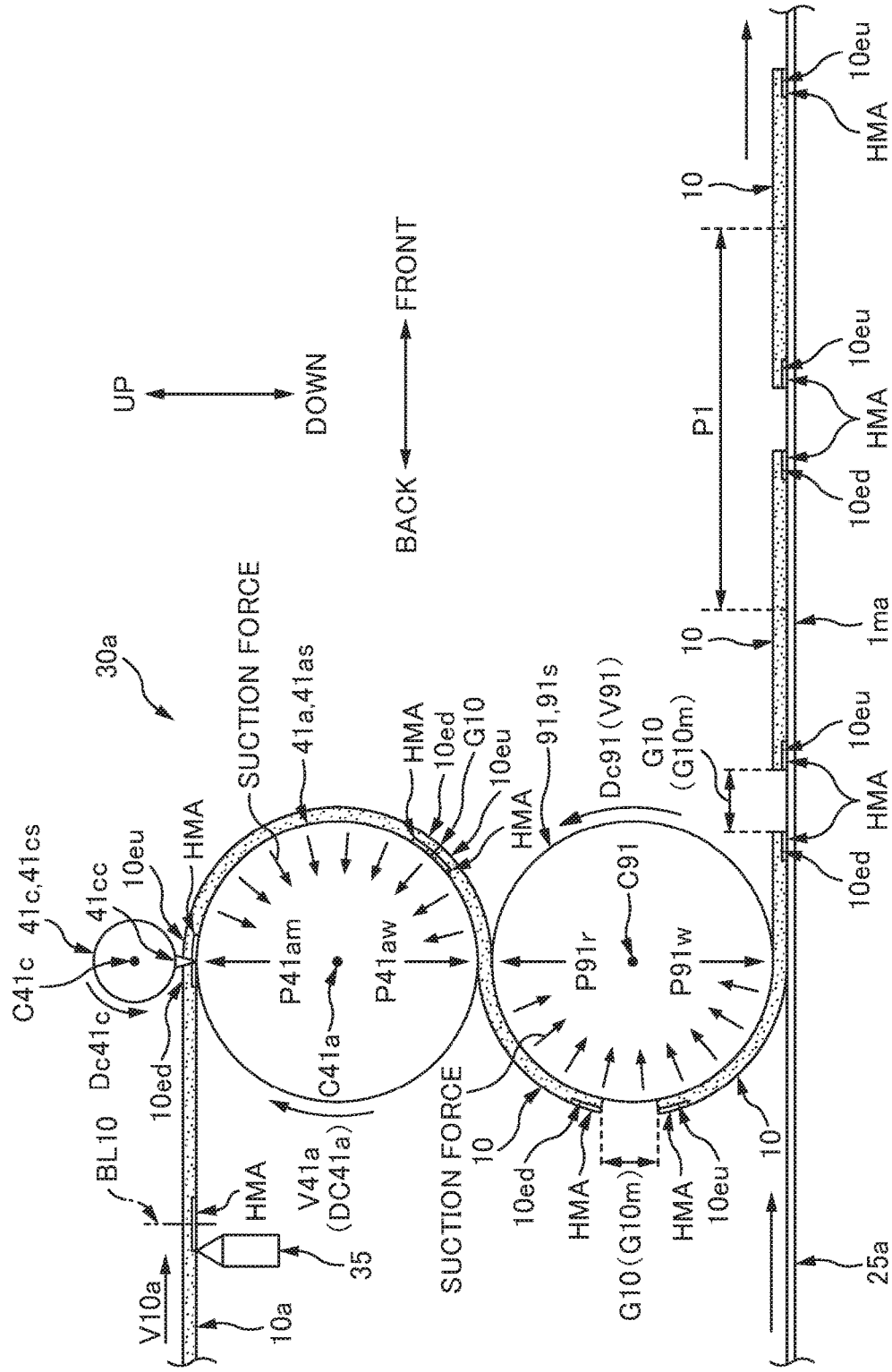
FIG. 7 is a schematic side view of the manufacturing apparatus 30a in which the transport device of the single-cut sheet of a second embodiment is incorporated.

FIG. 7 is an explanatory diagram of a transport device of a single-cut sheet in a second embodiment.

The transport device of a single-cut sheet in the second embodiment is also incorporated into a manufacturing apparatus 30a that manufactures an intermediate product 1ma of the diaper 1. This manufacturing apparatus 30a is used, for example, in a manufacturing line for a two-piece type diaper. Such a two-piece type diaper includes a front side portion, a crotch portion and a back side portion, and also includes an exterior sheet that constitutes the exterior of the diaper, and the absorbent main body 10. In the manufacturing apparatus 30a, a single-cut absorbent main body 10 is produced by being cut from the continuous body 10a of the absorbent main body to be transported from the upstream step, and the produced absorbent main body 10 is joined to a continuous sheet 25a of the exterior sheet to be transported from another upstream step. In the following description, the same components as those of the aforementioned first embodiment will be denoted by the same reference numerals, and the description thereof has been omitted in some cases.

As illustrated in FIG. 7, the manufacturing apparatus 30a includes an adhesive applying device 35, a cutter roll 41c, an anvil roll 41a and a joining roll 91.

The configuration of the adhesive applying device 35 is substantially the same as the case of the aforementioned first embodiment. In other words, also in this second embodiment, the adhesive HMA is applied to the continuous body 10a so as to straddle a boundary position BL10 between the adjacent absorbent main bodies 10, 10 in the direction of transport in the continuous body 10a of the absorbent main body. Thereby, the single-cut absorbent main body 10 which has been cut and produced by the cutter roll 41c and the anvil roll 41a after that becomes a state in which the adhesive HMA is applied to each of the end parts 10ed, 10eu in the longitudinal direction.

However, in the second embodiment, since the anvil roll 41a also serves as the aforementioned delivering roll 50 in the later-described enlargement process of the space G10 between the absorbent main bodies 10, 10, the adhesive HMA is applied to the surface facing the outer circumferential surface 41as of the anvil roll 41a, out the both surfaces of the continuous body 10a of the absorbent main body. In this respect, the second embodiment differs from the aforementioned first embodiment.

The configurations of the cutter roll 41c and the anvil roll 41a are also substantially the same as the case of the aforementioned first embodiment. In other words, the anvil roll 41a (corresponding to the first rotating body) is driven to rotate so as to be the same peripheral speed value V41a (m/s) as the transport speed V10a (m/s) of the continuous body 10a while holding the continuous body 10a of the absorbent main body to be transported from the upstream step on the outer circumferential surface 41as by suction force (corresponding to holding force) of the outer circumferential surface 41as, thereby transporting the continuous body 10a of the absorbent main body taking the direction of rotation Dc41a as a direction of transport. Further, the cutter roll 41c (corresponding to the fifth rotating body) also rotates along the direction of transport so that the cutter blade 41cc faces the boundary position BL10 every time the aforementioned boundary position BL10 of the continuous body 10a of the absorbent main body passes by the position of the cutter roll 41c. Accordingly, every time of this passing, the cutter blade 41cc faces the outer circumferential surface 41as of the anvil roll 41a, and at that time, the outer circumferential surface 41as functions as a surface-like receiving blade that receives the cutter blade 41cc. Consequently, the continuous body 10a of the absorbent main body is cut at the boundary position BL10. As a result, a single-cut absorbent main body 10 is produced on the outer circumferential surface 41as of the anvil roll 41a, and the absorbent main body 10 is transported taking the direction of rotation Dc41a as the direction of transport while being held on the outer circumferential surface 41as of the anvil roll 41a by the suction force, thus being delivered to the joining roll 91 at a delivering position P41aw in the direction of rotation Dc41a.

The joining roll 91 (corresponding to the second rotating body) is rotatably supported about the rotation shaft C91 along the CD direction and is driven to rotate by a servomotor (not shown) as a driving source. Further, an outer circumferential surface 91s of this joining roll 91 is also configured to be able to generate suction force. Furthermore, the outer circumferential surface 91s of the joining roll 91 faces the outer circumferential surface 41as of the anvil roll 41a while being closest thereto at the aforementioned delivering position P41aw, so that a position P91r corresponding to the aforementioned delivering position P41aw in the direction of rotation Dc91 of the joining roll 91 is a receiving position P91r where the joining roll 91 receives the absorbent main body 10 from the anvil roll 41a.

Thus, when each portion of the absorbent main body 10 passes by the aforementioned delivering position P41aw, the each portion is sequentially sucked and held on the outer circumferential surface 91s by the suction force of the outer circumferential surface 91s of the joining roll 91. Thereby, the absorbent main body 10 is delivered from the outer circumferential surface 41as of the anvil roll 41a to the outer circumferential surface 91s of the joining roll 91. Then, the joining roll 91 holds the received absorbent main body 10 by the suction force of the outer circumferential surface 91s and transports the absorbent main body 10 with its rotation taking the direction of rotation Dc91 of the joining roll 91 as the direction of transport to a delivering position P91w set at a predetermined position P91w in the direction of rotation Dc91.

Here, at the delivering position P91w, the continuous sheet 25a of the exterior sheet is transported in a state in which the direction of transport is along the direction of rotation Dc91 of the joining roll 91. First, when the downstream-side end part 10ed of the absorbent main body 10 passes by the aforementioned delivering position P91w, the end part 10ed is bonded to the continuous sheet 25a of the exterior sheet by the adhesive HMA of the end part 10ed, thereby delivering the end part 10ed to the continuous sheet 25a. Then, when each portion of the absorbent main body 10 passes by the position, the each portion is delivered from the outer circumferential surface 91s of the joining roll 91 to the continuous sheet 25a of the exterior sheet, and finally, when the upstream-side end part 10eu of the absorbent main body 10 passes by the aforementioned delivering position P91w, the end part 10eu is bonded to the continuous sheet 25a of the exterior sheet by the adhesive HMA of the end part 10eu. Accordingly, the absorbent main body 10 is delivered from the outer circumferential surface 91s of the joining roll 91 to the continuous sheet 25a. This produces an intermediate product 1ma in which a plurality of absorbent main bodies 10, 10 . . . is arranged and bonded to the continuous sheet 25a of the exterior sheet in the direction of transport.

Meanwhile, also in the second embodiment, the absorbent main body 10 immediately after being cut from the continuous body 10a of the absorbent main body by the cutter roll 41c and the anvil roll 41a is in a state of substantially abutting against another absorbent main body 10 located downstream in the direction of transport. In other words, these absorbent main bodies 10, 10 are arranged in the direction of transport in a state where there is substantially no space G10 between each other. Then, in this state where there is substantially no space G10, a pitch P10 in which the absorbent main bodies 10, 10 are arranged in the direction of transport is made smaller than a product pitch P1 in the direction of transport in which each absorbent main body 10 is to be placed on and bonded to the continuous sheet 25a of the exterior sheet.

Thus, in the manufacturing apparatus 30a, the aforementioned arrangement pitch P10 is enlarged to the product pitch P1 between the anvil roll 41a and the joining roll 91. This enlarges the space G10 between the absorbent main bodies 10, 10 from approximately zero to the target value G10m.

Here, this enlargement process is realized as follows. First, the peripheral speed value V91 in the direction of rotation Dc91 of the outer circumferential surface 91s of the joining roll 91 is made larger than the peripheral speed value V41a in the direction of rotation Dc41a of the outer circumferential surface 41as of the anvil roll 41a. Moreover, as described above, the anvil roll 41a substantially relatively immovably sucks and holds the absorbent main body 10 on the outer circumferential surface 41as. In addition, the adhesive strength of the adhesive HMA of each of the end parts 10eu, 10ed of the absorbent main body 10 also contributes to the holding of the absorbent main body 10 by the aforementioned anvil roll 41a.

Thus, as long as the upstream-side end part 10eu of the absorbent main body 10 in the direction of transport is located on the outer circumferential surface 41as of the anvil roll 41a, the absorbent main body 10 is transported at the peripheral speed value V41a of the outer circumferential surface 41as of the anvil roll 41a, so that the joining roll 91 transports the absorbent main body 10 while allowing a portion of the absorbent main body 10 which is located on the outer circumferential surface 91s of the joining roll 91 to relatively slide behind in the direction of transport with respect to the outer circumferential surface 91s.

After the adhesive HMA of the upstream-side end part 10eu of the absorbent main body 10 in the direction of transport is separated from the outer circumferential surface 41as of the anvil roll 41a and the end part 10eu moves to the outer circumferential surface 91s of the joining roll 91, the joining roll 91 transports the absorbent main body 10 at a larger peripheral speed value V91 of the roll 91. Accordingly, the space G10 between this absorbent main body 10 and the absorbent main body 10 which is adjacent on the upstream side and is produced by being cut is enlarged from approximately zero to the aforementioned target value G10m.

In the second embodiment, in a similar manner as the case of the aforementioned first embodiment, the adhesive HMA is applied only to each of the end parts 10eu, 10ed of the absorbent main body 10 in the direction of transport (longitudinal direction), and the adhesive HMA is not applied to portions other than each of the end parts 10eu, 10ed of the absorbent main body 10. However, the invention is not limited thereto. For example, the adhesive HMA may be applied to a portion between the end parts 10eu, 10ed of the absorbent main body 10. Further, not only in this second embodiment but also in the first embodiment, the adhesive HMA is applied to each of the end parts 10eu, 10ed of the absorbent main body 10 in the direction of transport. However, the invention is not limited thereto. For example, the adhesive HMA of the downstream-side end part 10ed in the direction of transport may be omitted.

Other Embodiments

Although embodiments of the present invention have been described above, the above-described embodiment is intended to facilitate the understanding of the present invention, and the present invention is not to be construed as being limited to the embodiment. And it is needless to say that various modifications and improvements can be made to the present invention without departing from the gist thereof, and equivalents thereof fall within the present invention. For example, the following modifications are possible.

In the aforementioned embodiment, the anvil roll 41a is used as a roll for holding the continuous body 10a of the absorbent main body by suction of the outer circumferential surface, and the cutter roll 41c is arranged so as to face the anvil roll 41a. However, the invention is not limited thereto. That is, in some cases, the cutter roll 41c may be used as a roll for sucking and holding the continuous body 10a on its outer circumferential surface, and the anvil roll 41a may be arranged so as to face the cutter roll 41c. In other words, the arrangement relationship between the cutter roll 41c and the anvil roll 41a may be reversed in FIG. 3A and FIG. 7.

In the aforementioned embodiment, although the disposable diaper 1 is exemplified as an absorbent article, the invention is not limited thereto as long as the absorbent article is an absorbent article that absorbs excreted fluid. For example, sanitary napkins and urine absorbing pads may be applicable.

In the aforementioned embodiment, the hot-melt adhesive is exemplified as an example of the adhesive HMA. However, the invention is not limited thereto. For example, as long as the adhesive has an adhesion property to the extent that can be separated from the outer circumferential surface 50s of the delivering roll 50 in the first embodiment or the outer circumferential surface 41as of the anvil roll 41a in the second embodiment, such adhesive can be used without any problem.

In the aforementioned second embodiment, the enlargement process has been performed between the anvil roll 41a and the joining roll 91. Here, the peripheral speed value V41a of the outer circumferential surface 41as of the anvil roll 41a and the peripheral speed value V91 of the outer circumferential surface 91s of the joining roll 91 are each constant over the entire circumference. In other words, since the rotational radius of the outer circumferential surface 41as (91s) of each roll 41a (91) is constant irrespective of the position in the circumferential direction, each peripheral speed value V41 (V91) is also a constant value without changing according to the position in the circumferential direction. On the other hand, in the case of the rotating drum device 60 of the first embodiment, the size of the turning radius of the holding surface 62 around the aforementioned rotation shaft C61 changes according to the position of the holding surface 62s in the longitudinal direction on the basis that the holding surface 62s of the holding pad 62 includes a plane region 62sp and inclined regions 62st2, 62st2 (FIGS. 4A and 4B). And along with this, the peripheral speed value V62 also changes according to the position of the holding surface 62s in the longitudinal direction. As the representative value of the peripheral speed value V62 of the holding surface 62s in such a case, for example, the average value of the peripheral speed value V62 over the entire length of in the longitudinal direction of the holding surface 62s. That is, the peripheral speed value V62 at each position in the longitudinal direction is integrated over the entire length in the longitudinal direction of the holding surface 62s, thereby obtaining an integrated value of the peripheral speed value V62. Then, this integrated value of the peripheral speed value V62 is divided by the overall length in the longitudinal direction of the holding surface 62s, thereby obtaining an average value of the peripheral speed value V62 of the holding surface 62s. By making the average value of the peripheral speed value V62 larger than the peripheral speed value V50 of the delivering roll 50, the space G10 between the absorbent main bodies 10, 10 can be enlarged to the target value G10m. Note that, the peripheral speed value V62 of the holding surface 62s for enlarging the space G10 to the target value G10m, that is, a target value V62m of the peripheral speed value V62 can be obtained as follows, for example. First, the aforementioned product pitch P1 is divided by the pitch P10 in which the absorbent main bodies 10, 10 . . . are arranged in a state where there is substantially no space G10 described above, and thus a divided value R (=P1/P10) is obtained. Next, by multiplying the peripheral speed value V50 of the delivering roll 50 by the divided value R, the target value V62m of the aforementioned peripheral speed value V62 can be obtained.

In the aforementioned first embodiment, the synchronization signal is used to synchronize the cutting operation of the cutter device 40 and the rotating operation of the rotating drum 61. Here, this synchronization signal will be described. The synchronization signal is generated, for example, by a rotary encoder (not shown) that detects the rotating operation of the cutter roll 41c. The synchronization signal is a signal consisting of a unit signal which is repeatedly outputted every time the cutter blade 41cc of the cutter roll 41c in FIG. 3A faces the outer circumferential surface 41as of the anvil roll 41a. In this example, the rotational angle signal constituted by a rotational angle value between 0° and 360° is used as the unit signal. Each time the unit signal is output, the rotating drum 61 rotates around the rotation shaft C61 by the rotation angle (60° in FIG. 3A) corresponding to a single holding pad 62, thereby allowing each holding pad 62 to pass by the receiving position P60r so as to correspond to each absorbent main body 10 in one-to-one correspondence. However, the unit signal of the synchronization signal is not limited to the signal indicated by the aforementioned rotational angle value of 0° to 360°. For example, the unit signal may be constituted by a digital value such as from 0 to 8191.

In the aforementioned embodiment, the upstream-side end part 10eu and the downstream-side end part 10ed of the absorbent main body 10 are given as an example of the upstream-side end part and the downstream-side end part in the single-cut sheet. The upstream-side end part 10eu described here is a divided area located on the most upstream side among a plurality of divided areas obtained by equally dividing the absorbent main body 10 into three or more (or five or more) areas in the longitudinal direction. For example, the divided area located on the most upstream side among nine divided areas obtained by equally dividing the absorbent main body 10 into nine areas in the longitudinal direction means the aforementioned upstream-side end part 10eu, or the divided area located on the most upstream side among seven divided areas obtained by equally dividing the absorbent main body 10 into seven areas in the longitudinal direction means the aforementioned upstream-side end part 10eu. Note that, this also applies to the downstream-side end part 10ed.

In the aforementioned embodiment, the adhesive HMA has been provided also in the most upstream part 10eue in the upstream-side end part 10eu. However, the invention is not limited thereto. That is, the adhesive HMA may be provided at least in a part of the upstream-side end part 10eu. For example, the adhesive HMA may be selectively provided in a portion excluding the most upstream part 10eue in the upstream-side end part 10eu. In other words, the most upstream part 10eue of the aforementioned upstream-side end part 10eu may be a non-applied portion where the adhesive HMA is not applied. This also applies to the downstream-side end part 10ed.

The invention claimed is:

1. A transport method of a single-cut sheet associated with an absorbent article, the method enlarging a space between single-cut sheets adjacent in a direction of transport, the single-cut sheets being produced by being sequentially cut from a continuous sheet that is transported in the direction of transport, the method comprising:
   a first transporting step of transporting the single-cut sheets taking a direction of rotation of a first rotating body as the direction of transport by rotating the first rotating body while holding the single-cut sheets on an outer circumferential surface with a holding force of the outer circumferential surface of the first rotating body, the single-cut sheets being each produced by being cut from the continuous sheet; and
   a second transporting step of transporting the single-cut sheets taking a direction of rotation of a second rotating body as the direction of transport by rotating the second rotating body while receiving and holding the single-cut sheets on an outer circumferential surface of the second rotating body, the single-cut sheets being transported from the first rotating body,
   in the first transporting step, an upstream-side end part of each of the single-cut sheets in the direction of transport being bonded to the outer circumferential surface of the first rotating body by adhesive provided at least in a part of the upstream-side end part, each of the single-cut sheets being transported in the direction of transport at a peripheral speed value of the first rotating body,
   in the second transporting step, in a state in which the second rotating body rotates at a peripheral speed value larger than the peripheral speed value of the first rotating body, and the upstream-side end part of each of the single-cut sheets is located on the outer circumferential surface of the first rotating body, the second rotating body transporting each of the single-cut sheets while allowing a portion of each of the single-cut sheets located on the second rotating body to relatively slide behind in the direction of transport with respect to the outer circumferential surface of the second rotating body on the basis that each of the single-cut sheets is transported in the direction of transport at the peripheral speed value of the first rotating body,
   after the adhesive of the upstream-side end part is separated from the outer circumferential surface of the first rotating body and the upstream-side end part moves from the outer circumferential surface of the first rotating body to the outer circumferential surface of the second rotating body, the second rotating body transporting the single-cut sheets at the peripheral speed value of the second rotating body,
   wherein
   a cutter device that cuts the continuous sheet and transports the single-cut sheets to the first rotating body is provided at an upstream side position of the first rotating body in the direction of transport,
   the cutter device includes a third rotating body and a fourth rotating body which rotate along the direction of transport with their outer circumferential surfaces facing each other,
   while the third rotating body holds on the outer circumferential surface the continuous sheet that is transported in the direction of transport, a blade-shaped cutter blade provided so as to protrude from the outer circumferential surface of one of the third rotating body and the fourth rotating body is received by the outer circumferential surface of the other of the third rotating body and the fourth rotating body to produce the single-cut sheets by being cut from the continuous sheet on the outer circumferential surface of the one rotating body, the third rotating body transports the single-cut sheets to the first rotating body by rotating while holding the produced single-cut sheets on the outer circumferential surface, and the adhesive is applied to one of two surfaces of the continuous sheet, the one facing toward the outer circumferential surface of the fourth rotating body.

2. The transport method according to claim 1, wherein the adhesive is provided at least in a most upstream-side part of each of the single-cut sheets in the direction of transport.

3. The transport method according to claim 1, wherein the fourth rotating body is a cutter rotating body including the cutter blade on the outer circumferential surface.

4. The transport method according to claim 1, wherein after a most upstream-side part of each of the single-cut sheets in the direction of transport moves from the third rotating body to the first rotating body, a most downstream-side part of each of the single-cut sheets in the direction of transport moves from the first rotating body to the second rotating body.

5. The transport method according to claim 4, wherein a circumference length of the outer circumferential surface of the first rotating body is longer than a length of each of the single-cut sheets in the direction of transport.

6. The transport method according to claim 4, wherein the circumference length of the outer circumferential surface of the first rotating body is twice or more the length of each of the single-cut sheets in the direction of transport.

7. The transport method according to claim 1, wherein the adhesive is provided also at least in a part of a downstream-side end part of each of the single-cut sheets in the direction of transport.

8. A transport method of a single-cut sheet associated with an absorbent article, the method enlarging a space between single-cut sheets adjacent in a direction of transport, the single-cut sheets being produced by being sequentially cut from a continuous sheet that is transported in the direction of transport, the method comprising:

a first transporting step of transporting the single-cut sheets taking a direction of rotation of a first rotating body as the direction of transport by rotating the first rotating body while holding the single-cut sheets on an outer circumferential surface with a holding force of the outer circumferential surface of the first rotating body, the single-cut sheets being each produced by being cut from the continuous sheet; and a second transporting step of transporting the single-cut sheets taking a direction of rotation of a second rotating body as the direction of transport by rotating the second rotating body while receiving and holding the single-cut sheets on an outer circumferential surface of the second rotating body, the single-cut sheets being transported from the first rotating body, in the first transporting step, an upstream-side end part of each of the single-cut sheets in the direction of transport being bonded to the outer circumferential surface of the first rotating body by adhesive provided at least in a part of the upstream-side end part, each of the single-cut sheets being transported in the direction of transport at a peripheral speed value of the first rotating body, in the second transporting step, in a state in which the second rotating body rotates at a peripheral speed value larger than the peripheral speed value of the first rotating body, and the upstream-side end part of each of the single-cut sheets is located on the outer circumferential surface of the first rotating body, the second rotating body transporting each of the single-cut sheets while allowing a portion of each of the single-cut sheets located on the second rotating body to relatively slide behind in the direction of transport with respect to the outer circumferential surface of the second rotating body on the basis that each of the single-cut sheets is transported in the direction of transport at the peripheral speed value of the first rotating body, after the adhesive of the upstream-side end part is separated from the outer circumferential surface of the first rotating body and the upstream-side end part moves from the outer circumferential surface of the first rotating body to the outer circumferential surface of the second rotating body, the second rotating body transporting the single-cut sheets at the peripheral speed value of the second rotating body, wherein the adhesive is provided also at least in a part of a downstream-side end part of each of the single-cut sheets in the direction of transport, each of the single-cut sheets is produced by being cut at a predetermined position of the continuous sheet in the direction of transport, and the position to be cut is included in an applied region to which the adhesive is applied in the continuous sheet.

9. A transport method of a single-cut sheet associated with an absorbent article, the method enlarging a space between single-cut sheets adjacent in a direction of transport, the single-cut sheets being produced by being sequentially cut from a continuous sheet that is transported in the direction of transport, the method comprising:

a first transporting step of transporting the single-cut sheets taking a direction of rotation of a first rotating body as the direction of transport by rotating the first rotating body while holding the single-cut sheets on an outer circumferential surface with a holding force of the outer circumferential surface of the first rotating body, the single-cut sheets being each produced by being cut from the continuous sheet; and a second transporting step of transporting the single-cut sheets taking a direction of rotation of a second rotating body as the direction of transport by rotating the second rotating body while receiving and holding the single-cut sheets on an outer circumferential surface of the second rotating body, the single-cut sheets being transported from the first rotating body, in the first transporting step, an upstream-side end part of each of the single-cut sheets in the direction of transport being bonded to the outer circumferential surface of the first rotating body by adhesive provided at least in a part of the upstream-side end part, each of the single-cut sheets being transported in the direction of transport at a peripheral speed value of the first rotating body, in the second transporting step, in a state in which the second rotating body rotates at a peripheral speed value larger than the peripheral speed value of the first rotating body, and the upstream-side end part of each of the single-cut sheets is located on the outer circumferential surface of the first rotating body, the second rotating body transporting each of the single-cut sheets while allowing a portion of each of the single-cut sheets located on the second rotating body to relatively slide behind in the direction of transport with respect to the outer circumferential surface of the second rotating body on the basis that each of the single-cut sheets is transported in the direction of transport at the peripheral speed value of the first rotating body, after the adhesive of the upstream-side end part is separated from the outer circumferential surface of the first rotating body and the upstream-side end part moves from the outer circumferential surface of the first rotating body to the outer circumferential surface of the second rotating body, the second rotating body transporting the single-cut sheets at the peripheral speed value of the second rotating body, wherein the holding force of the first rotating body occurs due to a suction operation of a plurality of suction holes formed on the outer circumferential surface, and in a part of the outer circumferential surface to which the upstream-side end part of each of the single-cut sheets faces, the suction holes are not provided on an upstream side of a portion facing to the adhesive.

10. A transport method of a single-cut sheet associated with an absorbent article, the method enlarging a space between single-cut sheets adjacent in a direction of transport, the single-cut sheets being produced by being sequentially cut from a continuous sheet that is transported in the direction of transport, the method comprising:

a first transporting step of transporting the single-cut sheets taking a direction of rotation of a first rotating body as the direction of transport by rotating the first rotating body while holding the single-cut sheets on an outer circumferential surface with a holding force of the outer circumferential surface of the first rotating body, the single-cut sheets being each produced by being cut from the continuous sheet; and a second transporting step of transporting the single-cut sheets taking a direction of rotation of a second rotating body as the direction of transport by rotating the second rotating body while receiving and holding the single-cut sheets on an outer circumferential surface of the second rotating body, the single-cut sheets being transported from the first rotating body, in the first transporting step, an upstream-side end part of each of the single-cut sheets in the direction of transport being bonded to the outer circumferential surface of the first rotating body by adhesive provided at least in a part of the upstream-side end part, each of the single-cut sheets being transported in the direction of transport at a peripheral speed value of the first rotating body, in the second transporting step, in a state in which the second rotating body rotates at a peripheral speed value larger than the peripheral speed value of the first rotating body, and the upstream-side end part of each of the single-cut sheets is located on the outer circumferential surface of the first rotating body, the second rotating body transporting each of the single-cut sheets while allowing a portion of each of the single-cut sheets located on the second rotating body to relatively slide behind in the direction of transport with respect to the outer circumferential surface of the second rotating body on the basis that each of the single-cut sheets is transported in the direction of transport at the peripheral speed value of the first rotating body, after the adhesive of the upstream-side end part is separated from the outer circumferential surface of the first rotating body and the upstream-side end part moves from the outer circumferential surface of the first rotating body to the outer circumferential surface of the second rotating body, the second rotating body transporting the single-cut sheets at the peripheral speed value of the second rotating body, wherein the holding force of the first rotating body occurs due to a suction operation of a plurality of suction holes formed on the outer circumferential surface, and on the outer circumferential surface of the first rotating body, the suction holes are not provided in a portion to which the adhesive of each of the single-cut sheets faces.

11. A transport method of a single-cut sheet associated with an absorbent article, the method enlarging a space between single-cut sheets adjacent in a direction of transport, the single-cut sheets being produced by being sequentially cut from a continuous sheet that is transported in the direction of transport, the method comprising:

a first transporting step of transporting the single-cut sheets taking a direction of rotation of a first rotating body as the direction of transport by rotating the first rotating body while holding the single-cut sheets on an outer circumferential surface with a holding force of the outer circumferential surface of the first rotating body, the single-cut sheets being each produced by being cut from the continuous sheet; and a second transporting step of transporting the single-cut sheets taking a direction of rotation of a second rotating body as the direction of transport by rotating the second rotating body while receiving and holding the single-cut sheets on an outer circumferential surface of the second rotating body, the single-cut sheets being transported from the first rotating body, in the first transporting step, an upstream-side end part of each of the single-cut sheets in the direction of transport being bonded to the outer circumferential surface of the first rotating body by adhesive provided at least in a part of the upstream-side end part, each of the single-cut sheets being transported in the direction of transport at a peripheral speed value of the first rotating body, in the second transporting step, in a state in which the second rotating body rotates at a peripheral speed value larger than the peripheral speed value of the first rotating body, and the upstream-side end part of each of the single-cut sheets is located on the outer circumferential surface of the first rotating body, the second rotating body transporting each of the single-cut sheets while allowing a portion of each of the single-cut sheets located on the second rotating body to relatively slide behind in the direction of transport with respect to the outer circumferential surface of the second rotating body on the basis that each of the single-cut sheets is transported in the direction of transport at the peripheral speed value of the first rotating body, after the adhesive of the upstream-side end part is separated from the outer circumferential surface of the first rotating body and the upstream-side end part moves from the outer circumferential surface of the first rotating body to the outer circumferential surface of the second rotating body, the second rotating body transporting the single-cut sheets at the peripheral speed value of the second rotating body,
wherein
the upstream-side end part of each of the single-cut sheets is bonded by the adhesive to another member associated with manufacture of the absorbent article.

* * * * *